(12) United States Patent
Robichaud et al.

(10) Patent No.: US 11,589,876 B2
(45) Date of Patent: Feb. 28, 2023

(54) SURGICAL GUIDE ASSEMBLY FOR PERFORMING A KNEE OSTEOTOMY PROCEDURE

(71) Applicant: LABORATOIRES BODYCAD INC., Québec (CA)

(72) Inventors: Jean Robichaud, St-Aubert (CA); Hugo Robichaud, Quebec (CA); Geoffroy Rivet-Sabourin, Stoneham (CA)

(73) Assignee: LABORATOIRES BODYCAD INC., Québec (CA)

( * ) Notice: Subject to any disclaimer, the term of this patent is extended or adjusted under 35 U.S.C. 154(b) by 66 days.

(21) Appl. No.: 16/610,446

(22) PCT Filed: Aug. 22, 2019

(86) PCT No.: PCT/CA2019/051147
§ 371 (c)(1),
(2) Date: Nov. 1, 2019

(87) PCT Pub. No.: WO2020/037418
PCT Pub. Date: Feb. 27, 2020

(65) Prior Publication Data
US 2021/0353304 A1 Nov. 18, 2021

Related U.S. Application Data

(60) Provisional application No. 62/722,403, filed on Aug. 24, 2018, provisional application No. 62/722,439, filed on Aug. 24, 2018.

(51) Int. Cl.
*A61B 17/88* (2006.01)
*A61B 17/15* (2006.01)
(Continued)

(52) U.S. Cl.
CPC ........ *A61B 17/151* (2013.01); *A61B 17/1764* (2013.01); *A61B 90/03* (2016.02); *A61B 2090/034* (2016.02)

(58) Field of Classification Search
CPC . A61B 17/151; A61B 17/1764; A61B 17/157; A61B 90/03; A61B 2090/034
See application file for complete search history.

(56) References Cited

U.S. PATENT DOCUMENTS

| 2,002,021 A | 5/1935 | Rouse |
| 5,620,448 A | 4/1997 | Puddu |

(Continued)

FOREIGN PATENT DOCUMENTS

| CN | 103393459 A | 11/2013 |
| CN | 207721848 U | 8/2018 |
| WO | WO-2015/003284 A2 | 1/2015 |

OTHER PUBLICATIONS

International Search Report and Written Opinion for Application No. PCT/CA2019/051147, dated Oct. 15, 2019.

(Continued)

*Primary Examiner* — Kevin T Truong
*Assistant Examiner* — Tracy L Kamikawa
(74) *Attorney, Agent, or Firm* — Marshall, Gerstein & Borun LLP

(57) ABSTRACT

A surgical guide assembly for performing a knee osteotomy procedure, the assembly comprising: a body for securing to a patient's tibia bone; and a plurality of guide modules removably attachable to the body, each guide module being adapted to receive a corresponding surgical tool and to guide the corresponding surgical tool along a predetermined path during the knee osteotomy procedure.

22 Claims, 14 Drawing Sheets

(51) Int. Cl.
*A61B 17/17* (2006.01)
*A61B 90/00* (2016.01)

(56) References Cited

U.S. PATENT DOCUMENTS

| | | | |
|---|---|---|---|
| 5,749,875 A | 5/1998 | Puddu | |
| 6,017,342 A | 1/2000 | Rinner | |
| 6,066,142 A | 5/2000 | Serbousek et al. | |
| 6,461,359 B1 | 10/2002 | Tribus et al. | |
| 7,794,467 B2 | 9/2010 | McGinley et al. | |
| 7,935,119 B2 | 5/2011 | Ammann et al. | |
| 8,083,746 B2 | 12/2011 | Novak | |
| 8,092,465 B2 | 1/2012 | Metzger et al. | |
| 8,137,406 B2 * | 3/2012 | Novak | A61B 17/68 |
| | | | 623/20.32 |
| 8,211,112 B2 | 7/2012 | Novak et al. | |
| 8,241,292 B2 | 8/2012 | Collazo | |
| 8,241,293 B2 | 8/2012 | Stone | |
| 8,337,507 B2 | 12/2012 | Lang et al. | |
| 8,388,690 B2 | 3/2013 | Singhatat et al. | |
| 8,409,209 B2 | 4/2013 | Ammann et al. | |
| 8,484,001 B2 | 7/2013 | Glozman et al. | |
| 8,594,395 B2 | 11/2013 | Roose et al. | |
| 8,632,547 B2 | 1/2014 | Maxson et al. | |
| 8,709,052 B2 | 4/2014 | Ammann et al. | |
| 8,753,348 B2 | 6/2014 | DiDomenico et al. | |
| 8,828,087 B2 | 9/2014 | Stone et al. | |
| 8,979,866 B2 | 3/2015 | Patel et al. | |
| 8,998,903 B2 | 4/2015 | Price et al. | |
| 9,014,835 B2 | 4/2015 | Azernikov et al. | |
| 9,072,555 B2 | 7/2015 | Michel | |
| 9,456,833 B2 | 10/2016 | Maxson et al. | |
| 9,480,490 B2 | 11/2016 | Meizger et al. | |
| 9,486,228 B2 * | 11/2016 | Saw | A61B 17/157 |
| 9,492,183 B2 * | 11/2016 | Wilkinson | A61B 17/02 |
| 9,603,605 B2 | 3/2017 | Collazo | |
| 9,622,759 B2 * | 4/2017 | Jansen | A61B 17/1757 |
| 9,687,261 B2 | 6/2017 | Serbousek et al. | |
| 9,707,023 B2 * | 7/2017 | Ammann | A61B 17/152 |
| 9,770,302 B2 | 9/2017 | Kang et al. | |
| 9,814,533 B2 | 11/2017 | Park et al. | |
| 9,833,245 B2 | 12/2017 | Maxson | |
| 9,877,758 B2 | 1/2018 | Michel | |
| 9,877,790 B2 | 1/2018 | Bojarski et al. | |
| 9,943,348 B2 | 4/2018 | Schelling | |
| 10,245,089 B2 | 4/2019 | Paik | |
| 2005/0209599 A1 | 9/2005 | Brunsvold | |
| 2006/0052795 A1 | 3/2006 | White | |
| 2007/0191848 A1 | 8/2007 | Wack et al. | |
| 2009/0082816 A1 | 3/2009 | Graham et al. | |
| 2011/0213376 A1 | 9/2011 | Maxson et al. | |
| 2013/0338673 A1 | 12/2013 | Keppler | |
| 2015/0051650 A1 | 2/2015 | Verstreken et al. | |
| 2015/0305752 A1 | 10/2015 | Eash | |
| 2016/0095634 A1 | 4/2016 | Meyer | |
| 2016/0113784 A1 | 4/2016 | Robichaud | |
| 2016/0192949 A1 * | 7/2016 | Robichaud | A61B 17/157 |
| | | | 606/87 |
| 2016/0235454 A1 | 8/2016 | Treace et al. | |
| 2016/0287266 A1 * | 10/2016 | Sikora | A61F 2/4081 |
| 2016/0324532 A1 * | 11/2016 | Montoya | A61B 17/15 |
| 2017/0325823 A1 | 11/2017 | Bake et al. | |
| 2017/0325826 A1 | 11/2017 | Bake et al. | |

OTHER PUBLICATIONS

International Search Report and Written Opinion for Application No. PCT/CA2019/051148, dated Oct. 24, 2019.
International Search Report and Written Opinion for Application No. PCT/CA2019/051149, dated Oct. 7, 2019.
International Search Report and Written Opinion for Application No. PCT/CA2019/051151, dated Oct. 22, 2019.
International Search Report and Written Opinion for Application No. PCT/CA2019/051153, dated Sep. 25, 2019.
International Search Report and Written Opinion for Application No. PCT/CA2019/051156, dated Sep. 30, 2019.
International Search Report and Written Opinion for Application No. PCT/CA2019/051157, dated Oct. 25, 2019.
Azernikov S. (2013) Inhomogeneous Axial Deformation for Orthopedic Surgery Planning. In: Csurka G., Kraus M., Mestetskiy L., Richard P., Braz J. (eds) Computer Vision, Imaging and Computer Graphics. Theory and Applications. VISIGRAPP 2011. Communications in Computer and Information Science, vol. 274, p. 69-85. Springer, Berlin, Heidelberg.

* cited by examiner

SURGICAL GUIDE ASSEMBLY FOR PERFORMING A KNEE OSTEOTOMY PROCEDURE

CROSS-REFERENCE TO RELATED APPLICATIONS

This application claims the benefit of U.S. Provisional Application No. 62/722,439, filed Aug. 24, 2018, entitled "SURGICAL GUIDE ASSEMBLY FOR PERFORMING A KNEE OSTEOTOMY PROCEDURE", and of U.S. Provisional Application No. 62/722,403, filed Aug. 24, 2018, entitled "SURGICAL KIT FOR KNEE OSTEOTOMIES AND CORRESPONDING PREOPERATIVE PLANNING METHOD", the entirety of which is herein incorporated by reference.

TECHNICAL FIELD

The technical field generally relates to tools used in knee osteotomy procedures, and more particularly in high tibial osteotomies.

BACKGROUND

Knee osteotomies are orthopedic procedures which aim to correct the alignment of knee joints to adjust pressure distribution. A high tibial osteotomy is a type of knee osteotomy which involves correcting the alignment of a knee joint by reconfiguring the mechanical axis of the tibia. Depending on the required correction angle, the high tibial osteotomy can be an open wedge osteotomy or a closed wedge osteotomy. In an open wedge osteotomy, a planar cut is made in the tibia below the knee, and the tibia bone is opened along the planar cut to form a wedge-shaped opening with a specified angle. In a closed wedge osteotomy, a wedge of bone having a specified angle is removed from the tibia bone below the knee, and the tibia bone is closed along the wedge. After the bone is opened or closed, it is retained in place by installing a fixation plate. The opening or closing effectively adjusts the angle of the tibia relative to the femur, thereby reconfiguring how pressure between the tibia and the femur is distributed in the knee.

Existing tools and procedures are limited in the accuracy and precision with which the alignment of the knee can be corrected. There is therefore much room for improvement.

SUMMARY

According to an aspect, there is provided a surgical guide assembly for performing a knee osteotomy procedure, the assembly comprising: a body for securing to a patient's tibia bone; and a plurality of guide modules removably attachable to the body, each guide module being adapted to receive a corresponding surgical tool and to guide the corresponding surgical tool along a predetermined path during the knee osteotomy procedure.

In at least one embodiment, the plurality of guide modules includes at least one drilling module removably securable to the body, each drilling module including a plurality of drill guides for cooperating with a plurality of corresponding drill bits to guide a position, depth, and angle thereof for forming drill holes in the patient's tibia bone in a predetermined configuration to weaken the patient's tibia bone in preparation for forming a cut therein.

In at least one embodiment, the drill guides are positioned and oriented relative to each other in a co-planar, parallel arrangement to define parallel drill holes in the patient's tibia bone in a common plane.

In at least one embodiment, the drill guides include a first group of parallel drill guides for creating a first plurality of drill holes in a first plane, and a second group of parallel drill guides for creating a second plurality of drill holes in a second plane.

In at least one embodiment, the body has a drill module interface adapted for selectively connecting one of the at least one drilling module to the body.

In at least one embodiment, the at least one drilling module includes a first drilling module for guiding the drill bits to form drill holes in a first parallel orientation in a common plane and a second drilling module for guiding the drill bits to form drill holes in a second parallel orientation different from the first parallel orientation, and in the same common plane.

In at least one embodiment, the plurality of guide modules further includes a cutting module secured to the body, the cutting module including a slot sized and shaped to receive a corresponding osteotome therein, and to guide the osteotome to cut the patient's tibia bone at a position, angle, and depth corresponding to an area of the patient's tibia bone weakened by the drilling module.

In at least one embodiment, the cutting module is positioned adjacent the patient's tibia bone, and the drilling module is positioned adjacent the cutting module.

In at least one embodiment, the cutting module is integrally formed with the body.

In at least one embodiment, the slot is positioned in alignment with the drill guides to allow the drill guides to guide the drill bits through the slot before entering the patient's tibia bone.

In at least one embodiment, the drilling module is removably attached to the cutting module via at least one connecting member extending therebetween, each connecting member being severable to allow the drilling module to be removed from the cutting module.

In at least one embodiment, the body includes an anchor module for anchoring the guide modules relative to the patient's bone, the anchor module including a removable module interface for selectively interfacing with one of the guide modules.

In at least one embodiment, the removable module interface includes at least one aperture for receiving at least one corresponding protrusion extending from a corresponding guide module.

In at least one embodiment, the body includes a first section and a second section detachably connected to the first section.

In at least one embodiment, the second section is configured to be secured to an anterior surface of the patient's tibia bone, and wherein the first section is configured to be secured to the patient's tibia bone laterally relative to the second section, the anchor module being provided in the first section.

In at least one embodiment, the first and second sections are independently securable relative to the patient's tibia bone to allow one of the first and second sections to be removed from the patient's tibia bone while the other one of the first and second sections remains secured to the patient's tibia bone.

In at least one embodiment, the anchor module comprises a proximal section positioned proximate the joint between the patient's femur and tibia bones, and a distal section spaced further away from the joint between the femur and tibia.

In at least one embodiment, the proximal and distal sections are separable from one another to allow them to move independently from each other while being secured to different sections of the patient's tibia bone.

In at least one embodiment, the assembly further including a spreader module configured to operate in cooperation with the anchor module for opening the patient's tibia bone along a planar cut formed therein.

In at least one embodiment, the spreader module comprising an upper arm and a lower arm pivotally connected to one another via a hinge, each one of the upper and lower arms having a load end and an effort end, the upper and lower arms being pivotable such that movement of the effort ends of the upper and lower arms towards one another moves the load ends of the upper and lower arms away from each other.

In at least one embodiment, the upper arm including a protrusion for engaging with the proximal section of the anchor module and the lower arm including a protrusion for engaging with the distal section of the anchor module.

In at least one embodiment, the plurality of guide modules further includes a predrilling module for predrilling holes in the patient's tibia bone for receiving fasteners to secure at least one of a plate and an implant to the patient's tibia bone.

In at least one embodiment, the predrilling module comprises a predrilling module body having a bone interface side for abutting against the patient's tibia bone, an operative side opposite the bone interface side and a plurality of drill guides extending from the operative side for guiding corresponding drill bits.

In at least one embodiment, the predrilling module further comprises an attachment mechanism for at least one of securing the predrilling module relative to the patient's tibia bone and assuring proper alignment of the predrilling module relative to the patient's tibia bone.

In at least one embodiment, the attachment mechanism comprises an attachment interface for interfacing with the removable module interface of the anchor module to attach the predrilling module to the anchor module, the attachment mechanism allowing the predrilling module to be positioned in only one position when attached to the anchor module.

In at least one embodiment, the attachment interface comprises two protrusions sized and shaped to engage in corresponding apertures of the anchor module.

In at least one embodiment, the protrusions are positioned to align with the anchor module while the patient's tibia bone is in a closed configuration to allow the predrilling module to engage with the patient's tibia bone and predrill holes prior to opening the bone.

In at least one embodiment, at least some of the plurality of guide modules are removably and interchangeably attachable to the body.

In at least one embodiment, the body includes a bone interface side for abutting against the patient's tibia bone, the bone interface side including a surface having contours complementary in shape to the surface contours of a predetermined area of the patient's tibia bone.

In at least one embodiment, the body is custom made according to an anatomy of the patient's tibia bone so as to be patient-specific.

In at least one embodiment, the body is made of a biocompatible material.

In at least one embodiment, the plurality of guide modules are made of a biocompatible material.

DETAILED DESCRIPTION

Figure 1A:
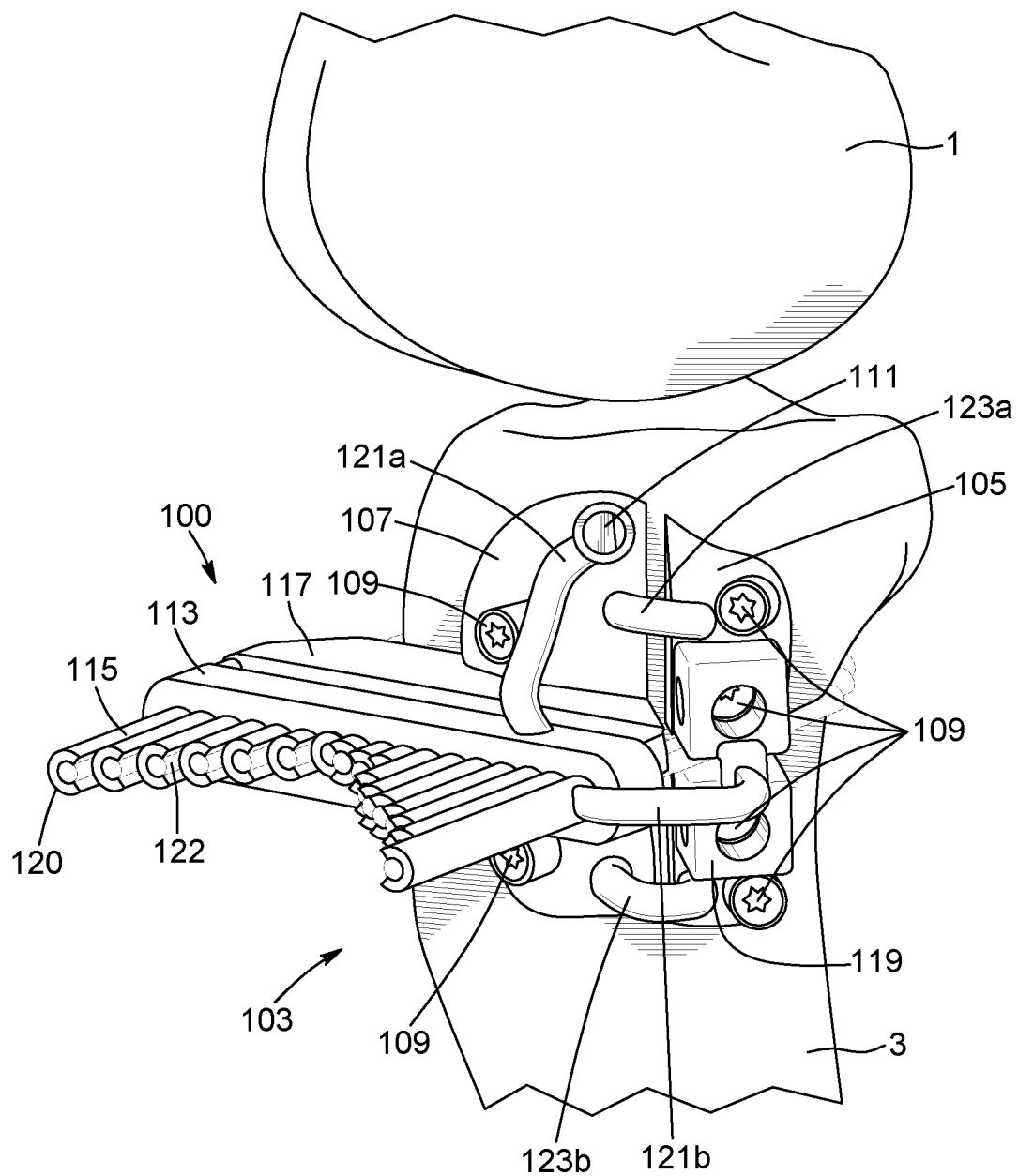
FIG. 1A is a perspective view of a surgical guide secured to a patient's tibia bone, according to an embodiment.
Figure 1B:
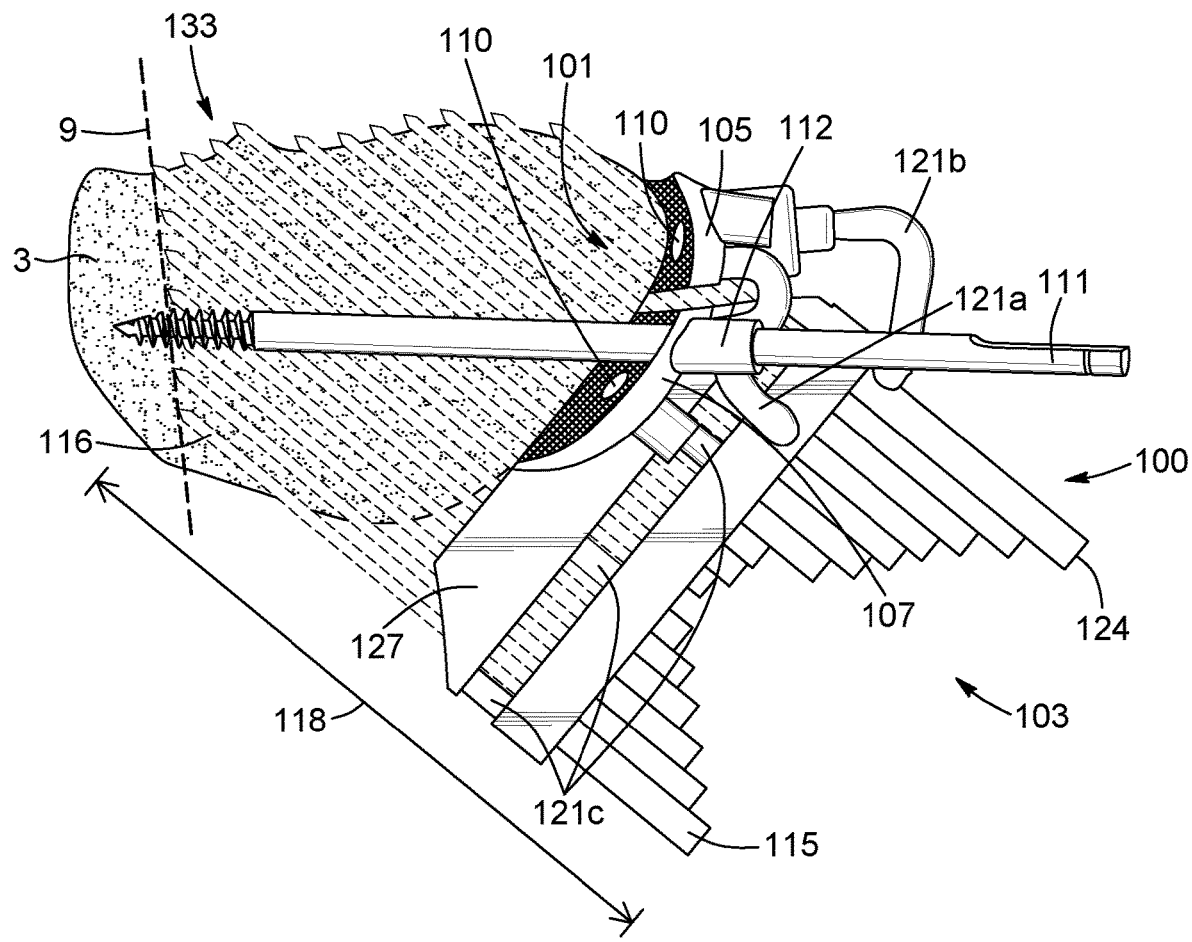
FIG. 1B is a top view of the surgical guide of FIG. 1A, showing drill holes formed through a cross section of the patient's tibia bone.

With reference to FIGS. 1A and 1B, a surgical guide 100 is provided. The surgical guide 100 is configured to be mounted to a patient's tibia bone 3 and includes a plurality of guide modules to guide various surgical tools used throughout the osteotomy procedure. The surgical guide 100 is patient-specific in that it is designed and manufactured according to the specific anatomy of a patient. In this fashion, the surgical guide 100 can be shaped and configured such that it can fit precisely on a predetermined position on the patient's bone 3 and be secured thereto to assure proper alignment of guides for various surgical tools. In the present embodiment, the surgical guide 100 has a body made from 3D printed plastic, although it is appreciated that other biocompatible materials compatible with other custom manufacturing methods are also possible.

The body of surgical guide 100 comprises a bone interface side 101 for facing the patient's bone 3, and an operative side 103 for facing away from the patient's bone 3. In the present embodiment, bone interface side 101 is configured to be positioned directly on the patient's bone, and comprises a surface having contours complementary in shape to the surface contours of a predetermined area of the patient's bone 3. In this configuration, bone interface side 101 can abut against the patient's bone, and key into a specific position thereon. In the present embodiment, bone interface side 101 comprises a solid surface, however it is appreciated that other configurations are possible. For example, the surface can be defined by an open lattice, and can comprise edges conforming to the contours of the patient's bone 3. Operative side 103 is provided opposite interface side 101 and includes a variety of components for interacting with surgical tools, as will be described in more detail hereinafter.

In the present embodiment, the body of surgical guide 100 is subdivided into two separable sections, including a lateral section 105 for securing relative to a lateral or medial surface of the patient's bone 3 and an anterior section 107 for securing relative to an anterior surface of the patient's bone 3. It is appreciated, however, that in other embodiments, more or fewer sections are possible to secure relative to different surfaces of the patient's bone 3 depending on surgical requirements. In the present embodiment, lateral section 105 and anterior section 107 are independently securable relative to the patient's bone 3. In this fashion, the lateral 105 or anterior 107 section can be removed from the patient's bone 3 when no longer needed, while the other section can remain secured in place. In the present embodiment, lateral 105 and anterior 107 sections are secured directly to the patient's bone. However, it is appreciated that in some embodiments, only one of the lateral 105 and anterior 107 need be affixed directly to the bone. For example, lateral section 105 can be affixed directly to the bone 3, whereas anterior section 107 can be removably attached to lateral section 105 such that it is secured relative the patient's bone 3 without being directly affixed thereto.

In the present embodiment, lateral and anterior sections 105, 107 comprise bone-conforming plates secured to the patient's bone 3 via fasteners. The fasteners comprise surgical screws 109 although it is appreciated that other types of fastening mechanisms are also possible. The screws 109 engage in the patient's bone 3 through canals 110 opening on the bone interface 101 and operative 103 sides of the surgical guide 100. The canals 110 comprise sidewalls extending along a length for guiding insertion of screws 109 through canals 110 at a specified angle and depth. In this fashion, screws 109 drilled into the patient's bone 3 through canals 110 can be guided into a predetermined position, orientation and depth such that they can secure patient-specific surgical guide 100 to the patient's bone 3 in an optimal fashion, and such that the screws 109 will not interfere with tools used during subsequent steps during the osteotomy procedure. The sidewalls of canals 110 can further be configured to abut against a head of screw 109 to block the screw 109 from being inserted too deep into the patient's bone 3.

In the present embodiment, a plurality of canals 110 are provided for securing the surgical guide 100 to the patient's bone 3 via a plurality of screws 109 at strategic locations. It is appreciated, however, that in other embodiments, a different number of screws 109 and canals 110 can be provided, and that they can be positioned and oriented differently depending on the patient's specific anatomy and according to the planned procedure. Moreover, in the present embodiment, each of screws 109 is the same size, but it is appreciated that in other embodiments, different sized screws can be used to secure different parts of the surgical guide 100, and that the canals 110 can be sized and shaped accordingly. Finally, although the screws 109 are guided by canals 110 in the present embodiment, it is appreciated that other screw-guiding mechanisms are possible in other embodiments.

As mentioned above, lateral 105 and anterior 107 sections are separable from one another. In the present embodiment, lateral 105 and anterior 107 sections are generally disjointed from one another and are connected via connecting members. In other words, lateral 105 and anterior 107 sections are not directly fused together, and instead comprise separate spaced-apart sections removably secured to one another at a finite number of fixed points. In this configuration, each of lateral 105 and anterior 107 sections define two separate bone-contacting surfaces including two bone-conforming plates on bone interface side 101 of surgical guide 100. It is appreciated, however, that in other embodiments, lateral 105 and anterior 107 sections can together form a single coherent surface or plate for contacting the bone 3.

Connecting members 121, 123, can be provided to removably connect different sections of the surgical guide 100. In the present embodiment, the lateral 105 and anterior 107 sections are connected to one another at three fixed points via connecting members 121*b*, 123*a* and 123*b*. The connecting members 121*b*, 123*a*, 123*b* are stems comprising narrow strands of rigid material connected at a first end to the lateral section 105 and at a second end to the anterior section 107. The connecting members 121*b*, 123*a*, 123*b* are fused to lateral 105 and anterior 107 sections and/or are formed as integral parts thereof. In this fashion, lateral 105 and anterior 107 sections can be rigidly connected to one another and can be disconnected by respectively severing each of connecting members 121*b*, 123*a*, 123*b*. Connecting members 121, 123 are configured such that an intermediate portion thereof is spaced away from surgical guide 100 and/or the patient's bone 3, thereby allowing the connecting members 121, 123 to be readily severed using a severing tool (such as a saw or scissors, for example) while minimizing a risk of damaging surgical guide 100 or bone 3. In the present configuration, connecting members 121*b*, 123*a*, 123*b* loop away from the surgical guide 100 and comprise a rounded intermediate section spaced away from surgical guide 100. Although a particular configuration of connecting members 121, 123 has been shown, it is appreciated that other configurations are possible. In other embodiments, connecting members 121, 123 can have different shapes, and can include different connecting elements. For example, in some embodiments, instead of being fused and/or an integral part of lateral 105 and/or anterior 107 sections, connecting members 121, 123 can be separate pieces removably engageable in lateral 105 and/or anterior 107 sections. As can be further appreciated, in other embodiments, a different number of connecting members 121, 123 can be provided, and they can be positioned differently.

As mentioned above, the surgical guide 100 comprises a plurality of guide modules to guide various surgical tools used throughout the osteotomy procedure. Each guide module can perform a different function for assisting with various tasks throughout an osteotomy procedure. Some modules can form integral parts of the lateral 105 and/or anterior 107 sections secured directly to the patient's bone 3, whereas other modules can be independent elements which can be secured to relative to the patient's bone 3 by attaching to lateral 105 and/or anterior 107 sections. Although a particular set of modules will be described in detail hereinafter, it is appreciated that other modules and combinations thereof are possible depending on the requirements of the surgical procedure. Moreover, although some modules are described as performing particular functions, it is appreciated that some modules can perform two or more functions and/or have other advantages or uses not explicitly described herein, but that would be readily understood by a person of skill in the art upon reading the present disclosure.

Security Pin Guide Module

In the present embodiment, a security pin guide module is provided for guiding insertion of a corresponding security pin or rod 111 into the patient's bone 3. Security pin guide module is an integral part of body of surgical guide, and comprises a security pin guide 112 formed therein. More specifically, security pin guide 112 is provided on anterior section 107 of surgical guide 100, although it is appreciated that other configurations are possible. In the present embodiment, security pin guide 112 is positioned proximate a top portion of anterior section 107 and comprises a canal to guide an angle of security pin 111 as it is inserted into the patient's bone 3. The pin guide 112 is angled such that when the security pin 111 is inserted into the patient's bone 3 it runs parallel to the tibial plateau. The security pin 111 is made from a rigid, biocompatible material, such as stainless steel or titanium, and can be screwed into the patient's bone 3. Once inserted into the patient's bone 3, the security pin 111 can remain in place for the remainder of the osteotomy procedure to protect the tibial plateau from fracturing. Accordingly, the security pin guide module can be configured to be removable from security pin 111 once the security pin 111 is installed. For example, pin guide 112 can be configured such that security pin 111 can slide therethrough unobstructed, allowing pin 111 to slide out from pin guide 112 when the security pin guide module is removed, for example when the anterior section 107 is removed from the patient's bone 3. Other configurations of pin 111 and pin guide 112 are also possible.

Drilling Module

A drilling module 113 is provided to assist in creating drill holes 116 in the patient's bone 3 in preparation for forming a cut therein. In the present embodiment, the drilling module 113 is removably secured to the body of surgical guide 100 via connecting members 121. More specifically, a plurality of connecting members 121a, 121b, and 121c extend between the drilling module 113 and the body of surgical guide 100, securing the drilling module 113 to lateral 105 and anterior 107 sections of surgical guide 100. The connecting members 121 comprise stems of rigid material forming integral parts of both surgical guide 100 and drilling module 113, and drilling module 113 can be removed from surgical guide 100 by severing stems of connecting members 121.

Figure 5:
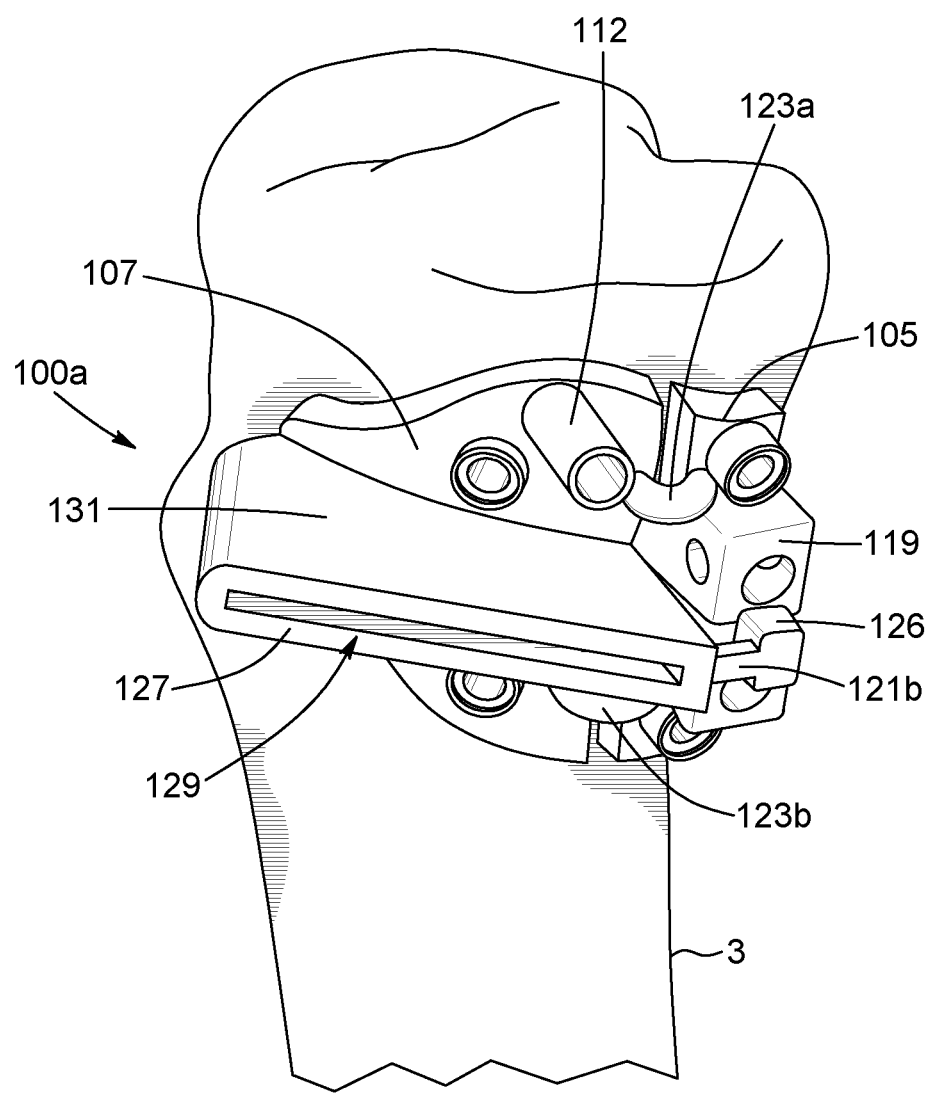
FIG. 5 is a perspective view of a surgical guide secured to the patient's tibia bone, according to an alternate embodiment in which the osteotome guide acts as an interface for connecting a removable drilling module.
Figure 6A:
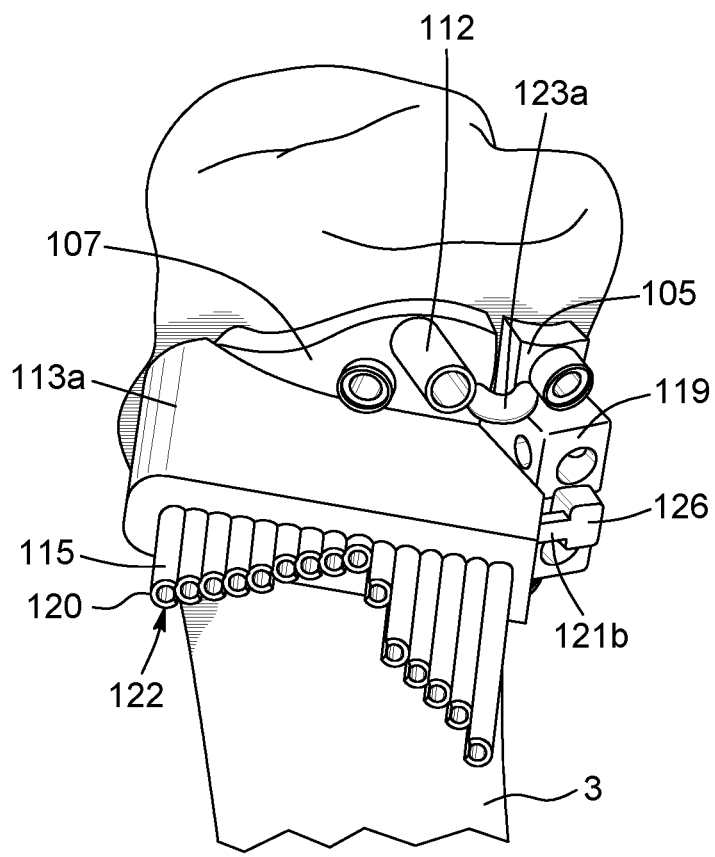
FIG. 6A is a perspective view of the surgical guide of FIG. 5, including a first removable drilling module secured thereto via the osteotome guide.
Figure 6B:
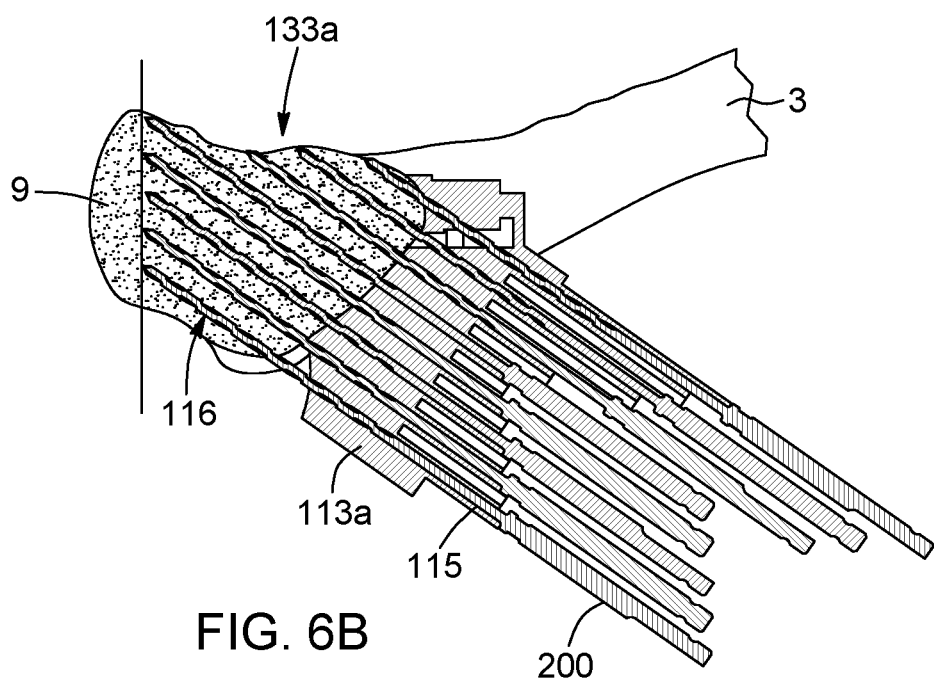
FIG. 6B is a top view of the surgical guide and drilling module of FIG. 6A, showing drill bits forming drill holes through a cross section of the patient's tibia bone.
Figure 7A:
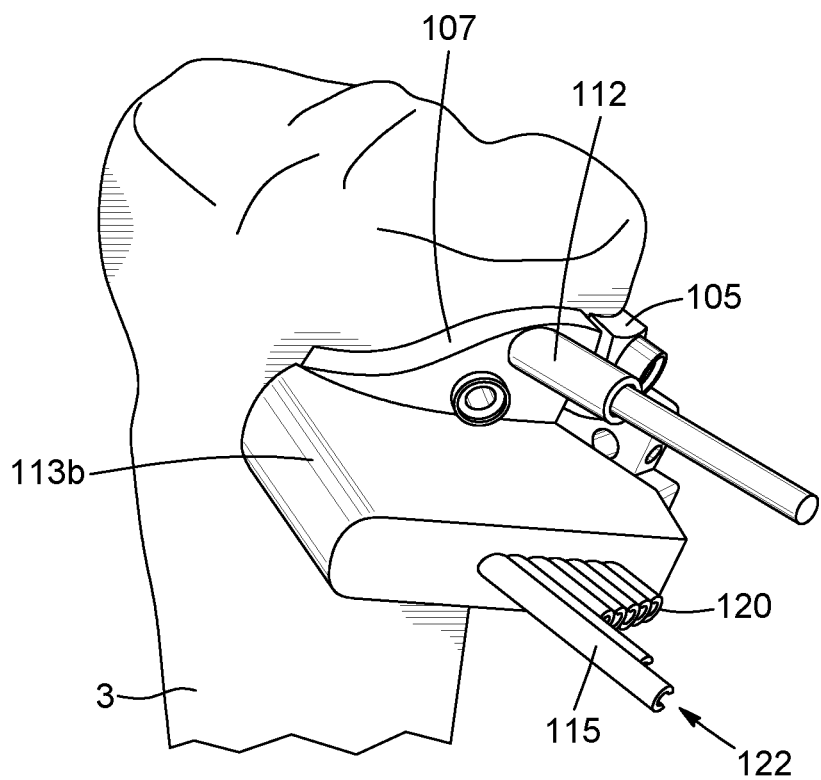
FIG. 7A is a perspective view of the surgical guide of FIG. 5, including a second removable drilling module secured thereto via the osteotome guide.
Figure 7B:
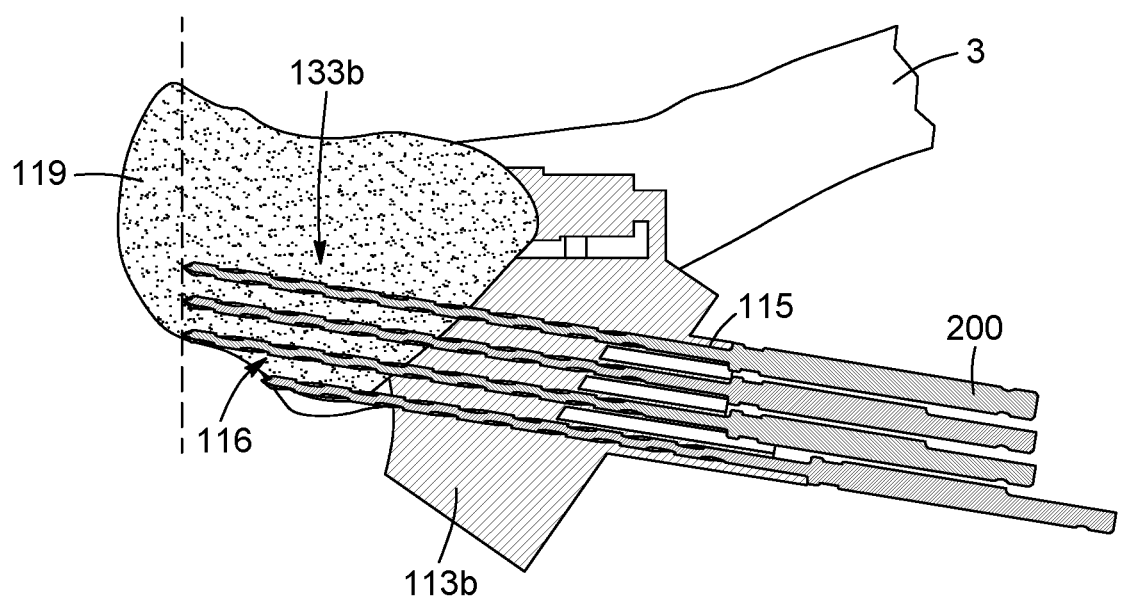
FIG. 7B is a top view of the surgical guide and drilling module of FIG. 7A, showing drill bits forming drill holes through a cross section of the patient's tibia bone.

Although in the present embodiment the drilling module 113 is secured to the body of surgical guide 100 via severable stems, it is appreciated that other connection mechanisms are possible to secure and position drilling module 113 relative to the patient's bone. For example, drilling module can engage with body of surgical guide 100 via fasteners, and/or can engage directly to the patient's bone. In an embodiment, for example as shown in FIG. 5, the drilling module 113 can clip onto a predetermined position on surgical guide 100. In the embodiment of FIG. 5, surgical guide 100a comprises a drill module interface 131 in the form of a tongue element. A corresponding removable drill guide module, such as drill guide modules 113a and 113b shown in FIGS. 6A and 6B, can comprise a slot or groove sized and shaped to receive tongue 131 therein. In this configuration, drill guide module 113a, 113b can clip onto a fixed position on surgical guide 100 by sliding over tongue 131. It is appreciated that in alternate embodiments, drilling module 113 can comprise a tongue for fitting in a corresponding groove in surgical guide 100 and/or a combination of tongue and grooves for fitting with corresponding tongue and groves in surgical guide 100.

Referring back to FIGS. 1A and 1B, the drilling module 113 comprises a plurality of drill guides 115 for cooperating with corresponding drill bits to guide a position, depth, and angle thereof to form drill holes 116 in the patient's bone 3 in a predetermined configuration. In the present embodiment, the drill guides 115 each comprise a guiding element accessible from the operative side 103 of surgical guide 100. The guiding element comprises a guide barrel 120 extending from the operative side 103 of surgical guide 100, although it is appreciated that other types of guide elements are also possible. The guide barrel 120 extends along a lengthwise axis, between a proximal end proximate the bone interface side 101 of guide 100, and a terminal end 124 on the operative side 103 of guide 100. The guide barrel 120 comprises sidewalls defining a hollow interior in the form of a guide tunnel 122 extending through the guide barrel 120 along the lengthwise axis thereof, and opening on the bone interface side 101 and operative side 103 of guide 100. The guide tunnels 122 are sized and shaped to receive a corresponding drill bit therein, allowing the drill bit to slide in and out of barrel 120, while sidewalls of barrel 120 constrain movement of the drill bit to a predetermined depth, position, and orientation relative to the patient's bone.

Figure 2A:
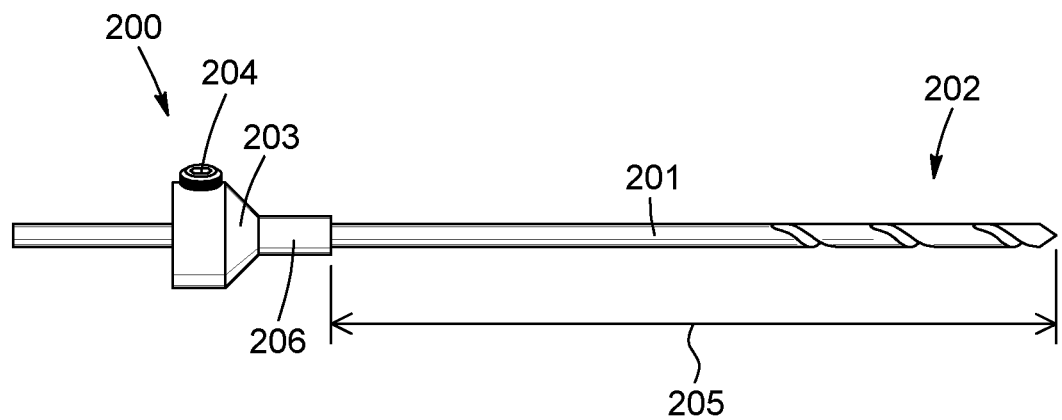
FIG. 2A is a side view of a drill bit configured to cooperate with corresponding drill guides in the surgical guide of FIG. 1A, according to an embodiment.
Figure 2B:
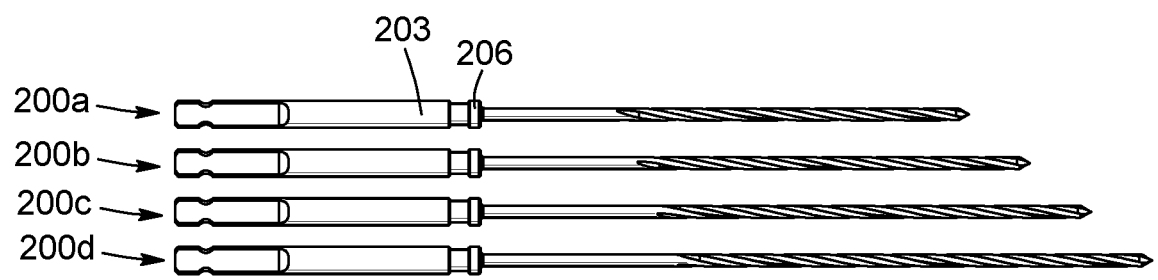
FIG. 2B is a side view of drill bits according to alternate embodiments having depth guides permanently secured relative to their cutting ends.

With reference to FIG. 2A, a drill bit 200 configured to cooperate with drill guide is shown according to an embodiment. The drill bit 200 comprises a drill bit body 201 extending along a length, and terminating at a cutting end 202. A depth guide 203 is provided on the drill bit body 201 and spaced away from the cutting end 202, effectively defining an operative length 205 of drill bit 200. In the present embodiment, depth guide 203 is removably secured to drill bit body 201 via fastener 204, allowing operative length 205 of drill bit 200 to be adjusted by loosening fastener 204 and sliding depth guide 203 to a desired location along the length of the drill bit body 201. It is appreciated, however, that in other embodiments, depth guide 203 can be permanently affixed to, and/or form an integral part of, drill bit body 201, effectively defining a fixed predetermined operative length 205. For example, as shown in FIG. 2B, drill bits 200a, 200b, 200c and 200d having respective fixed lengths of 80 mm, 90 mm, 100 mm and 110 mm are shown. Each drill bit comprises a depth guide 203 permanently secured relative to cutting end 202. As can be appreciated, a collection of fixed drill bits can be provided as part of a kit, and each bit can be identified via markings, and/or via color coding. In some embodiments, the markings and/or color coding can match with corresponding marking and/or color coding on the drill guides 115 in the drilling module 113.

With reference now to FIGS. 1A, 1B, 2A and 2B, depth guide 203 comprises an abutment member 206 for limiting an insertion depth of drill bit 200 in guide barrel 120. When operative length 205 of drill bit 200 is fully inserted into guide barrel 120, the abutment member 206 abuts against terminal 124, effectively preventing further insertion of drill bit 200. As can be appreciated, in this configuration, drill bit 200 can only be inserted into guide barrel 120 at a fixed insertion depth 118 relative to the terminal end 124. The position of terminal end 124 relative to the patient's bone 3 thus defines the penetration depth of drill bit 200 into the patient's bone 3. Accordingly, the length of guide barrel 120 determines the bone penetration depth of drill bit 200: a longer guide barrel 120 results in a shallower bone penetration depth of drill bit 200, and a shorter guide barrel results in a deeper bone penetration depth. Similarly, the position and orientation of the guide barrel 120 defines the position and orientation at which the drill bit 200 penetrates the patient's bone 3.

In the present embodiment, a plurality of drill guides 115 are provided for cooperating with a calibrated drill bit 200 having a fixed operative length 205. The drill guides 115 comprise guide barrels 120 positioned and arranged to create drill holes 116 in a predefined pattern to weaken the patient's bone 3 in preparation for a planar cut. More specifically, the drill guides 115 are positioned and oriented in a co-planar, parallel arrangement to define parallel drill holes 116 in the patient's bone 3 in a common plane 133. The guide barrels 120 of drill guides 115 are sized based on the specific geometry of the patient's bone 3, such that the drill holes 116 cover a majority of a cross section of the patient's bone 3, while leaving a non-weakened section to eventually form a hinge along which the patient's bone 3 can be opened. More specifically, the guide barrels 120 are positioned such that drill holes define a hinge axis 9 at a border between weakened and non-weakened areas of the patient's bone 3 in the common plane 133. As can be appreciated, hinge axis 9 can be oriented depending on the type and position of opening to be formed in the patient's bone 3 as determined according to a preoperative plan, to correct the mechanical axis of the patient's bone 3 as needed. In the present embodiment, hinge axis 9 is a straight line, but it is appreciated that other shapes are also possible.

Although in the present embodiment the drilling module 113 is configured to create drill holes 116 in a parallel orientation, it is appreciated that in other embodiments, the drilling module 113 can be configured such that some or all drill holes do not run parallel to one another. For example, the drill holes 116 can be grouped into two or more arrangements which intersect with one another. Although different groups of drill holes can be guided by the same drilling module 113, it is appreciated that in some embodiments, two or more drilling modules 113 can be provided, for example to create drill holes 116 in different arrangements, to weaken the patient's bone 3 in different steps/stages, and/or to allow drill bits to be inserted at different angles of approach. Where a plurality of drilling modules 113 are provided, they can be positioned and/or attached on the same section of the guide 100, or can be positioned on different sections of the guide 100, for example to drill on different faces of the patient's bone 3 and/or allow drill bits to be inserted at different orientations, for example to facilitate drilling holes in a position which would otherwise be more difficult to access.

For example, as shown in FIGS. 5, 6A, 6B, 7A, and 7B, surgical guide 100a can be configured with an anterior section 107 having a drill module interface 131 for connecting one or more removable drilling modules 113 thereto. A first drilling module 113a can be attached thereto to guide drill bits 200 to form drill holes 116 in a first parallel orientation 133a in the common plane 133 in the patient's bone. The first drilling module 113a can subsequently be removed, and in its place a second drilling module 113b can be attached to the same position on anterior section 107 via drill module interface 131. The second drilling module 113b can then guide drill bits 200 to form drill holes 116 in a second parallel orientation 133b different from the first parallel orientation 133a, and in the same plane 133. As can be appreciated, the two drilling modules 113a, 113b can allow for weakening the patient's bone 3 along the plane 133 in two phases and by inserting drill bits 200 at different orientations. This can, for example, allow a complete area of the patient's bone 3 to be weakened in preparation for cutting the patients bone, while reducing the size of the tissue incision required to access the patient's bone 3 to perform the procedure.

Figure 8A:
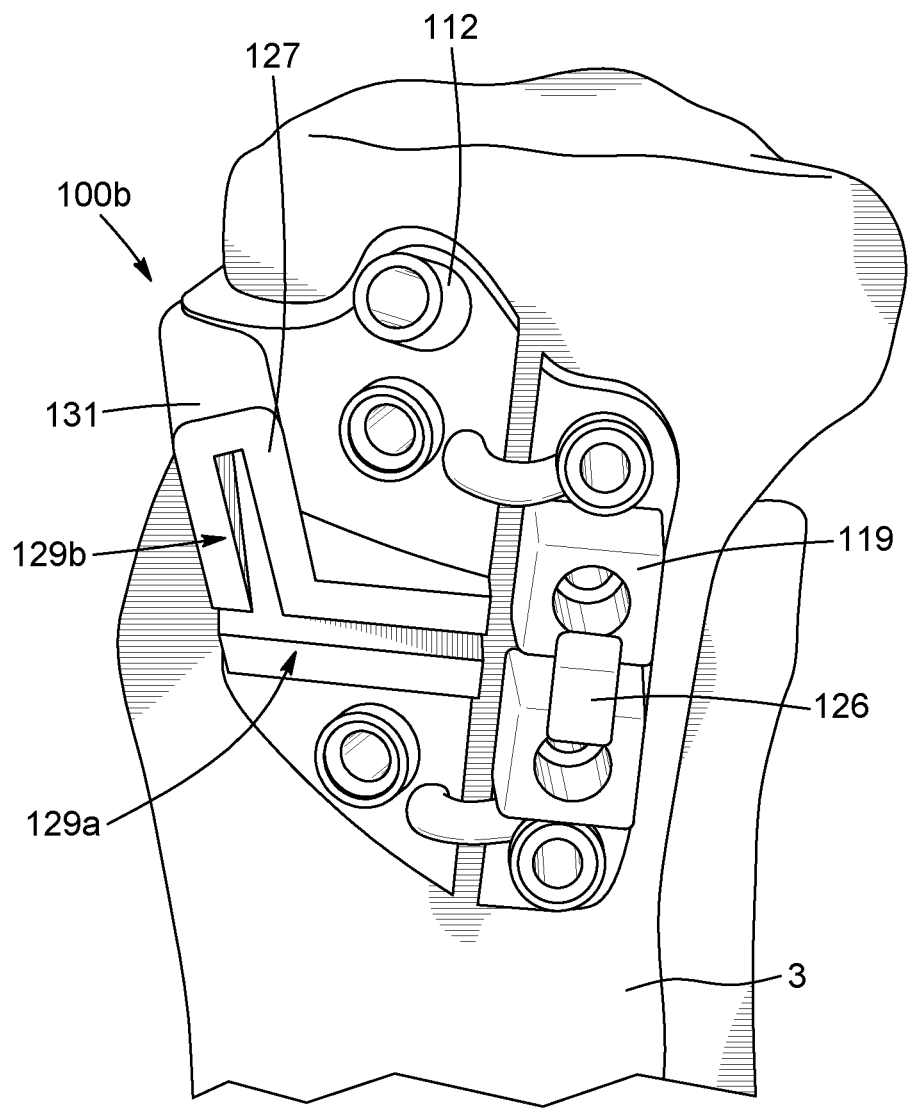
FIG. 8A is a perspective view of a surgical guide secured to the patient's tibia bone, according to an alternate embodiment in which the osteotome guide is configured to form a biplanar cut in the patient's bone.

Finally, although in the presently described embodiments the drilling module 113 is configured to guide drill holes 116 in a common plane 133, it is appreciated that in other embodiments, the drilling module can be configured to guide drill holes 116 into two or more planes depending on the requirements of the surgical procedure. For example, with reference to FIGS. 8A, 8C, and 8D drilling module 113 can comprise a first group of parallel drill guides 115a for creating a first plurality of drill holes 116 in a first plane 133, and a second group of parallel drill guides 115b for creating a second plurality of drill holes 116 in a second plane 135. As can be appreciated, the first plane 133 is not parallel to second plane 135 and is substantially perpendicular thereto, allowing to weaken the bone 3 to eventually form a biplanar cut 5a, 5b therein.

As can be appreciated, in some embodiments, a single drilling module 113 can be configured to create all the necessary drill holes to weaken the bone 3 in planes 133, 135 in preparation for forming biplanar cuts 5a, 5b. However, in other embodiments, two or more drilling modules 113 can be provided to create the necessary drill holes in planes 133, 135 in phases. For example, in the embodiment shown in FIGS. 8A, 8B, 8C, and 8D, two drilling modules 113a and 113b are provided. A first drilling module 113a can be secured to drill module interface 131 to create drill holes 116 in the first plane 133 in a first parallel orientation 133a. The drilling module 113a includes a cover element 137 for covering openings in the drill module interface 131 extending along the direction of the second plane 135. Once the drill holes have been formed in the first plane 133, the drilling module 113a can be removed, and a second drilling module 113b can be secured to the drill module interface 131. The second drilling module 113b is provided with a first group of drill guides 115a for drilling holes 116 in the first plane 133 in a second parallel orientation 133b different from the first parallel orientation 133a, thereby completing the required weakening of the bone in the first plane 133. The second drilling module 113b is further provided with a second group of drill guides 115b for drilling holes 116 in the second plane 135. In the present embodiment, the second group of drill guides 115b in the second drilling module 113b are sufficient to weaken the bone to form the second planar cut 5b. It is appreciated, however, that in other embodiments, further drill guides can be provided to cut in the second plane 135 in different parallel orientations.

Although in the embodiment described above, modules 113a and 113b are described as "first" and "second" modules, it is appreciated that their order of use can be inversed depending on the requirements of the surgical procedure. Moreover, although two modules were described, it is appreciated that in other embodiments, subsequent modules can be provided to further weaken the bone via drill holes 116 in different parallel orientations and/or in different planes as required. Moreover, in some embodiments, a cover element can be provided to cover opening in the drill module interface 131 extending along the direction of the first plane 133, for example in a drilling module configured to drill holes only in the second plane 135.

Cutting Module

Referring back to FIGS. 1A and 1B, a cutting module 117 is provided to assist in cutting the patient's bone 3. In the present embodiment, the cutting module 117 comprises an osteotome guide 127 for guiding a corresponding osteotome to cut the patient's bone 3 at predetermined position, orientation and depth. The guide 127 is configured to guide osteotome to create a planar cut in the patient's bone 3 in the area weakened by the drill holes 116 formed using the drilling module 113. The cutting module 117 is provided in anterior section 107 of guide 100—in other words, the cutting module 117 is integrally formed with the body of the surgical guide 100—and is affixed directly to the patient's bone via fasteners 109. It is appreciated, however, that in other embodiments, the cutting module 117 can be removably attached to the lateral 105 and/or anterior 107 sections of the surgical guide 100.

Although in the present embodiment a single cutting module 117 is shown, it is appreciated that two or more cutting modules can be provided in other embodiments. For example, in some embodiments, two or more cutting modules can be provided to help create a single planar cut in two or more stages. In some embodiments, a first cutting module can be configured to create a first planar cut in a first direction, and a second cutting module can be configured to create a second planar cut in a second direction. The cutting modules can be permanently or removably affixed relative to the same area of the patient's bone 3, and/or can be removably or permanently affixed relative to different areas of the patient's bone 3, for example to access the bone 3 from different positions.

The osteotome guide 127 comprises a body extending between a bone-contacting end on the bone interface side 101 of surgical guide 100, and a terminal end on operative side 103 of surgical guide 100. The body has a planar aperture or slot 129 extending therethrough and opening on the bone-contacting end and the terminal end. The slot 129 is sized and shaped to receive a corresponding osteotome therein, and to guide the osteotome to cut the patient's bone 3 at a position, angle, and depth corresponding to the area of the patient's bone 3 weakened by the drilling module 113. More specifically, osteotome can slide in and out of slot 129, while sidewalls around the aperture constrict the movement of osteotome to the correct position and angle to form the desired cut. Similarly, an abutting member of osteotome is configured to abut against terminal end of the osteotome guide 127 to limit an insertion depth of the osteotome. As can be appreciated, osteotome guide 127 can have visual indications provided thereon to further help guide osteotome visually and/or to indicate a type of osteotome to be used with guide 127.

In the present embodiment, in order to guide the osteotome to cut the area of the patient's bone 3 weakened by drilling module 113, the osteotome guide 127 is positioned in alignment with the drill guides 115. More specifically, the cutting module 117 is positioned adjacent the patient's bone 3, and the drilling module 113 is positioned adjacent the cutting module 117, such that the drill guides 115 open in alignment with the slot 129 in the osteotome guide 127. In this configuration, drill guides 115 guide drill bits 200 through the slot 129 in osteotome guide 127 before entering the patient's bone 3, thereby assuring that drill bits 200 and osteotome operate in the same plane 133. In the present configuration, cutting module 117 is affixed directly to patient's bone 3, while drilling module 113 is removably attached to cutting module 117. Drilling module 113 can thus be removed after drill holes 116 have been formed, providing the osteotome with direct access to cutting module 117. It is appreciated that other configuration are possible which can still allow drill bits 200 and osteotome to operate in the same plane. For example, in some embodiments, both drilling module 113 and cutting module 117 can be removably attachable to surgical guide 100. Drilling module 113 can be attached first to created drill holes 116. Drilling module 113 can be subsequently removed, and cutting module 117 can be attached to the same are of guide 100 as drilling module 113, allowing cutting module 117 to guide the osteotome in the same plane as the drill holes 116.

Figure 8B:
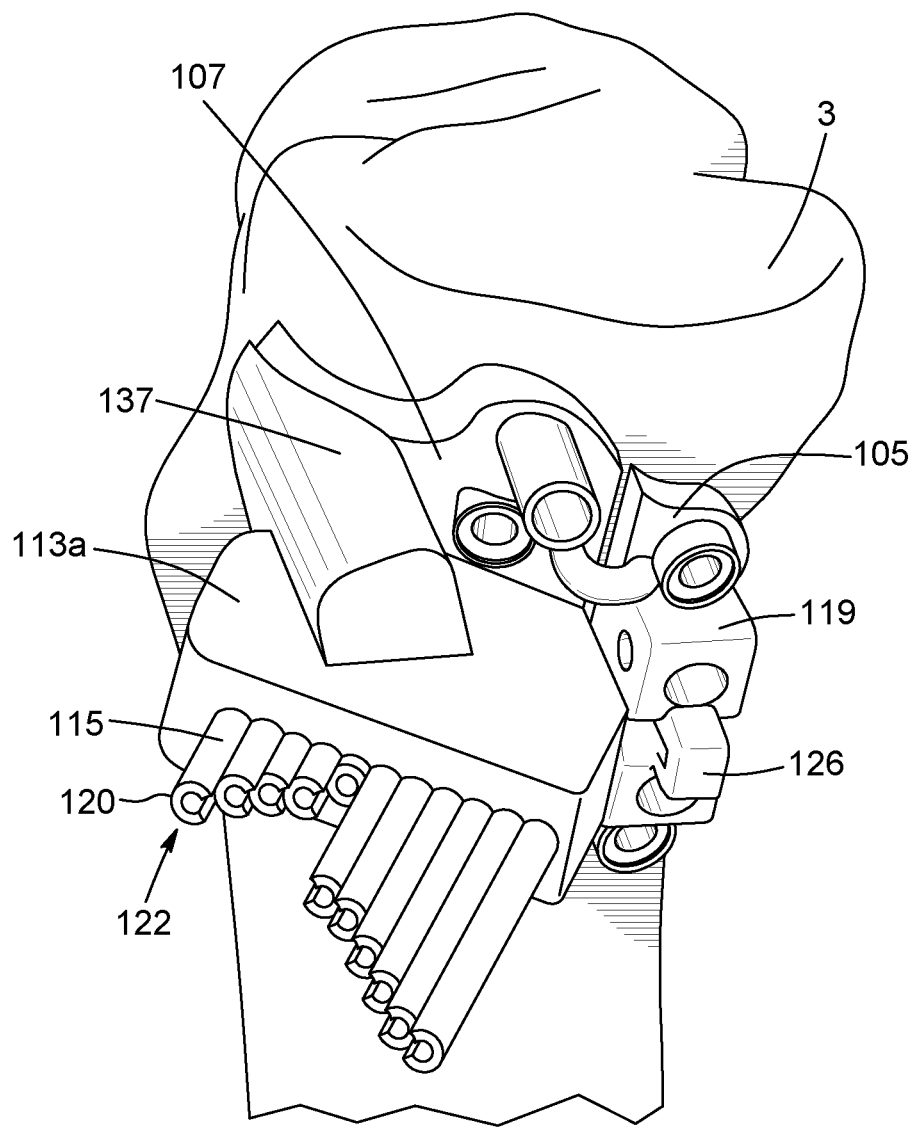
FIG. 8B is a perspective view of the surgical guide of FIG. 8A, including a first removable drilling module secured thereto via the osteotome guide, the first removable drilling module being configured to drill along a first plane.
Figure 8C:
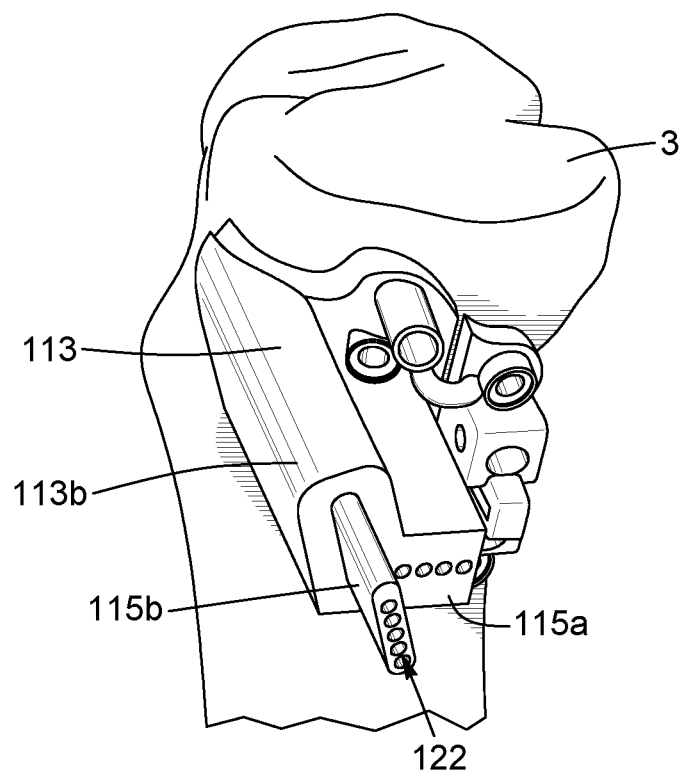
FIG. 8C is a perspective view of the surgical guide of FIG. 8A, including a second removable drilling module secured thereto via the osteotome guide, the second removable drilling module being configured to drill along the first plane and a second plane.
Figure 8D:
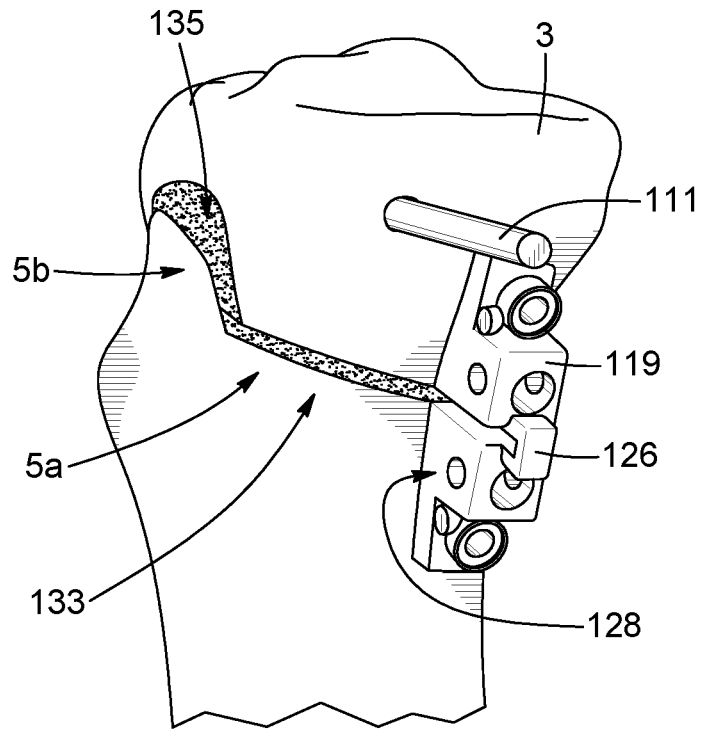
FIG. 8D is a perspective view of the patient's tibia bone with the anterior section of surgical guide of FIG. 8A removed, showing the biplanar cut formed in the patient's tibia bone.

In the present embodiment, the cutting module 117 is configured to guide osteotome to create a single planar cut 5 in the patient's bone 3, however it is appreciated that in other embodiment, the guide can be configured to create two or more cuts and/or cuts having a contour or curve. For example, with reference to FIGS. 8A and 8C, surgical guide 100b comprises an osteotome guide 127 configured with first 129a and second 129b slots for guiding osteotome to cut the patient's bone to create two planar cuts 5a and 5b along two different planes 133, 135. As can be appreciated, although two slots 129a and 129b are provided, use of the second slot 129b can be optional, allowing the same guide 100b to be compatible with both procedures involving single planar cuts 5 and biplanar cuts 5a, 5b. For example, as shown in FIGS. 8B and 8D, a drilling module 113a can be provided which includes drill guides 115 in only the first plane 133, whereas a cover element 137 covers the slots 129b in the second plane 135. In this fashion, the bone is only weakened along the first plane 133, and cut 5a can be formed in said plane. Additionally or alternatively, when manufactured for such procedures, the slot 129b in guide 100b can be covered to prevent an osteotome from being inserted therein. As can be appreciated, the guide 100b can still include the section of tongue of drill module interface 131 which extends along the plane where slot 129b once extended. In this fashion, the shape of drill module interface 131 can be the same regardless of whether or not a second plane is to be cut. This can allow for the same general shape/configuration of surgical guide 100b to be used for different types of surgical procedures involving single or biplanar cuts, and similarly allows for the same general shape/configuration of drilling modules 113 to be used. This can simplify the manufacturing and design of surgical guide 100 and corresponding modules, as the same shape can be used for all procedures types, yet simply adapted to conform the anatomy of the patient's bone 3.

Anchor Module

Figure 3A:
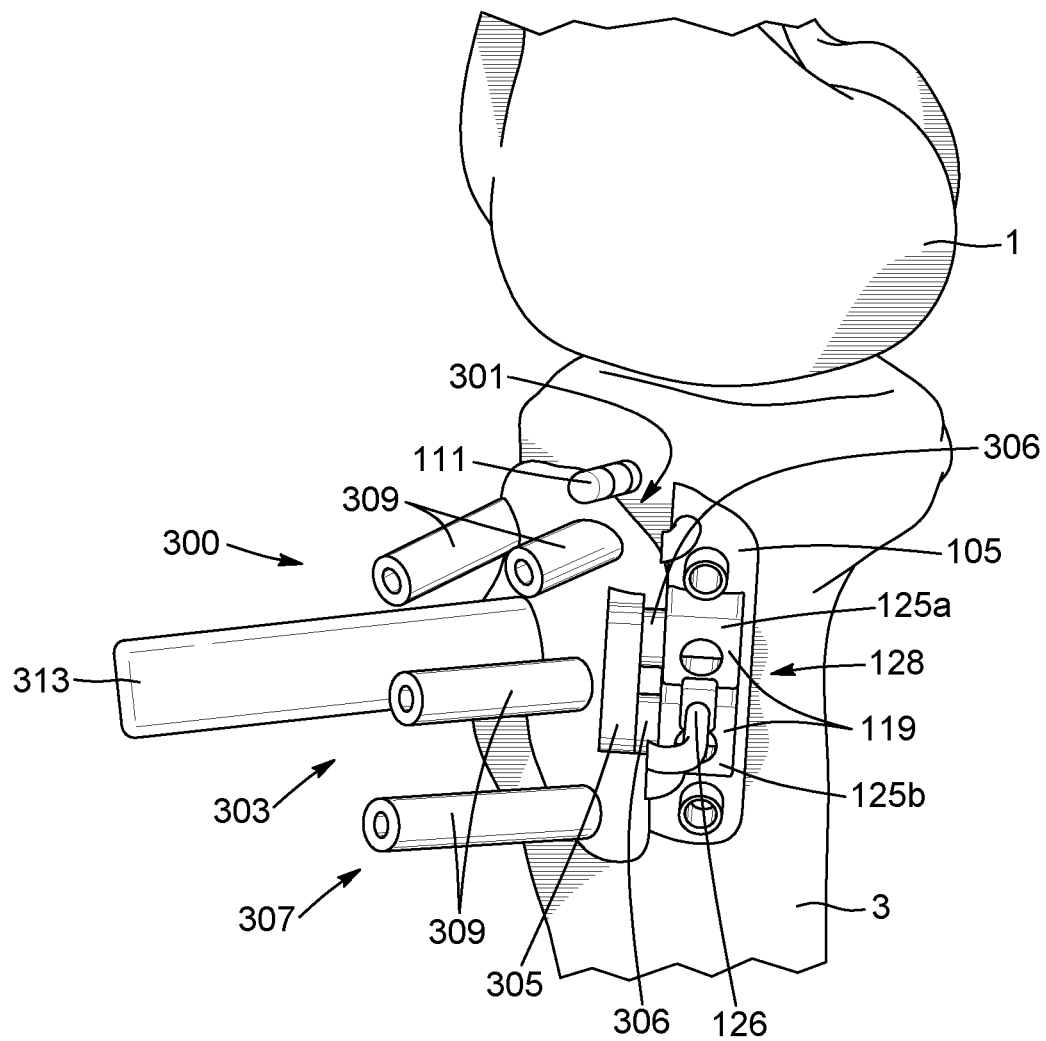
FIGS. 3A and 3B are respectively medial and anterior perspective views of a predrilling module secured to an anchor module on the patient's tibia bone, according to an embodiment.

With reference now to FIG. 3A, an anchor module 119 is provided to anchor removable guide modules relative to the patient's bone 3. In the present embodiment, anchor module 119 is provided in the lateral section 105 of the surgical guide 100, but it is appreciated that in other embodiments, anchor module 119 can be provided in a different section of guide 100. Moreover, in some embodiments, a plurality of anchor modules can be provided. The anchor module 119 is affixed directly to the patient's bone 3 via fasteners 109 and comprises a removable module interface 128 for interfacing with removable modules. The anchor module can thus act as a secure base to which other modules can be removably attached, allowing the removable modules to be properly aligned relative to the patient's bone 3 at relevant steps during the surgical procedure. In the present embodiment, the removable module interface 128 comprises apertures for receiving corresponding protrusions extending from a removable module, although it is appreciated that other removable connection interfaces are possible.

In the present embodiment, the anchor module 119 comprises two sections for providing two distinct anchoring points. More specifically, the anchor module 119 comprises a proximal section 125a positioned proximate the joint between the patient's femur 1 and tibia 3 bones, and a distal section 125b spaced further away from the joint between the femur 1 and tibia 3. The proximal 125a and distal 125b sections are separable from one another, allowing them to move independently while being secured to different sections of the patient's bone 3. In the present embodiment, proximal 125a and distal 125b sections are secured to one another via connecting member 126. The connecting member 126 can be severed to separate proximal 125a and distal 125b sections and allow them to move independently with different sections of bone. For example, in the present embodiment, proximal 125a and distal 125b sections are positioned on the patient's bone 3 on opposite sides of the planar cut formed by drilling module 113 and cutting module 117. After the planar cut is formed, connecting member 126 can be severed to separate proximal 125a and distal 125b sections. The bone 3 can be opened along the planar cut, with the proximal 125a and distal 125b sections moving away from one another while being respectively connected to the bone 3 above and below the opening formed in the bone 3. In this fashion, the proximal section 125a can provide an anchoring point above or proximal the opening in the bone 3, while the distal section 125b provides an anchoring point below or distal the opening in the bone 3. It is appreciated that other positions and configurations of anchor module 119 and corresponding sections are possible, depending on the surgical procedure. It is further appreciated that the separable sections of anchor module 119 can be connected to one another via different removable connection mechanisms.

Predrilling Module

Figure 3B:
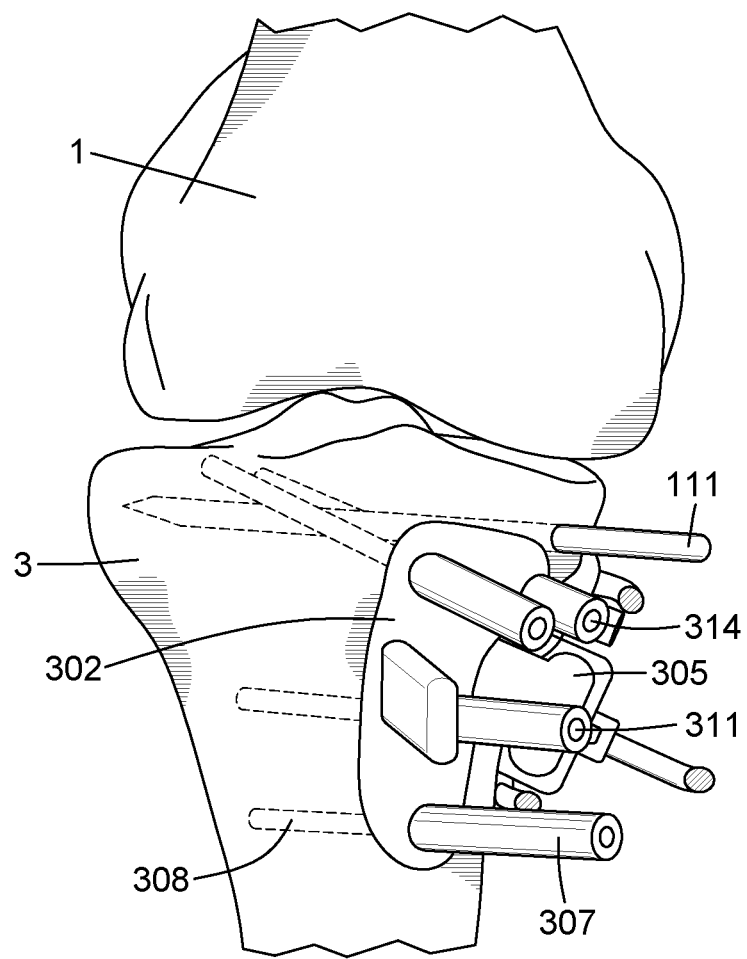

With reference to FIGS. 3A and 3B, a predrilling module 300 is provided for predrilling holes in the patient's bone 3 for eventually receiving fasteners to secure a plate or other implant to the patient's bone 3. The predrilling module 300 is patient-specific in that it is custom made according to the anatomy of the patient's bone 3 and according to a preoperative plan. In this fashion, the predrilling module 300 can be configured to precisely fit on a predetermined position of the patient's bone 3 to assure proper alignment, and to assist in drilling holes in the patient's bone 3 in predetermined positions, orientations and depths.

In the illustrated embodiment, the predrilling module 300 comprises a body 302 having a bone interface side 301 and an operative side 303. The bone interface side 301 comprises a bone-contacting surface having contours complementary in shape to the surface contours of the patient's bone 3. In this configuration, bone interface side 301 can abut against the patient's bone 3, and key into a specific position thereon. In the present embodiment, bone interface side 301 comprises a solid surface, however it is appreciated that other configurations are possible. For example, the surface can be defined by an open lattice, and can comprise edges conforming to the contours of the patient's bone 3.

The operative side 303 is provided opposite the bone interface side 301 and comprises a plurality of drill guides 307 extending therefrom for guiding corresponding drill bits. In the present embodiment, the drill guides 307 each comprise a guide barrel 309 extending from the body of the predrilling module 303 at a predetermined angle along a lengthwise axis and terminating at a terminal end 314. The guide barrel 309 comprises sidewalls defining a hollow interior in the form of a guide tunnel 311 extending through the guide barrel 309 along the lengthwise axis thereof and opening on the bone interface side 301 and operative side 303 of predrilling module 303. The guide tunnels 311 are sized and shaped to receive a corresponding drill bit therein, allowing the drill bit to slide in and out of barrel 309, while sidewalls of barrel 309 constrain movement of the drill bit to a predetermined depth, position, and orientation relative to the patient's bone 3. An abutting member on the drill bit can limit an insertion depth of an operative end of the drill bit into the barrel 309 as it abuts with terminal end 314 of guide barrel 309. As can be appreciated, in this configuration, the length of barrel 309 can limit insertion depth of a drill bit and assure the depth of drill holes formed therewith.

The plurality of drill guides 307 are configured to cooperate with a calibrated drill bit having a fixed operative length. The guide barrels 309 of the drill guides 307 are sized, positioned and oriented to create drill holes 308 in a predefined pattern for receiving fasteners to secure an implant, such as plate, to the patient's bone 3. As will be described in more detail hereinafter, the implant to be secured can be patient-specific and can be designed to be affixed using different types of fasteners. Based on the anatomy of the patient's bone 3, a preoperative plan can define a configuration of fasteners, including size, depth, orientation, and position, such that the implant can be affixed optimally. The drill guides 307 can thus be configured to guide drill bits to form drill holes 308 in preparation for receiving the configuration of fasteners defined in the preoperative plan. For example, the length of each guide barrel 309 can be adjusted to limit the insertion depth of the drill bit, creating drill holes 308 with different predetermined depths. Similarly, the position an orientation of guide barrels 309 can be adjusted to define drill holes 308 which extend at different angles and positions. Finally, diameters of guide tunnels 311 can be adjusted to accommodate drill bits of different diameters to create drill holes of different sized for accommodating different sizes of fasteners.

In the present embodiment, the predrilling module 300 is configured to predrill holes 308 in the patient's bone 3 prior to a surgical alteration of the bone's geometry. The predrilling module 300 is thus configured to account for the drill holes 308 moving as the geometry of the bone is altered during surgery, such that the drill holes 308 will be in alignment with the fasteners of an implant once the bone alterations are complete. For example, in the context of a high-tibial open-wedge osteotomy procedure, the predrilling module 300 can be configured to predrill holes while the patient's bone 3 is in a closed configuration (i.e. before the patient's bone 3 is opened along the planar cut formed using the drilling 113 and cutting 117 modules). In this configuration, the guide barrels 309 are positioned to form drill holes 308 which will eventually align with the location of fasteners for affixing an implant once the patient's bone 3 is opened along the planar cut to an opened configuration. As can be appreciated, the required position of drill holes 308 can be determined by modelling the patient's bone 3, virtually opening the bone model to a desired opening angle, and virtually positioning an implant and corresponding fasteners on the bone model to set final positions of the drill holes 308. The bone model can be subsequently closed virtually to determine corresponding initial positions of the drill holes 308. The predrilling module 300 can then be designed according to the initial positions of the drill holes 308.

As shown in FIGS. 3A and 3B, predrilling module 300 comprises an attachment/alignment mechanism 305 for securing the predrilling module 300 relative to the patient's bone 3 and/or for assuring proper alignment of the predrilling module 300 relative to the patient's bone 3. In the present embodiment, the attachment/alignment mechanism 305 comprises an attachment interface for interfacing with removable module interface 128 in anchor module 119. The attachment/alignment mechanisms 305 is configured such that the predrilling module 300 can attach to anchor module 119 in only one position/orientation, thus assuring that predrilling module 300 is properly aligned once it is attached to anchor module 119. For example, in the present embodiment, the attachment interface comprises two protrusions or pins 306 sized and shaped to engage in corresponding apertures in anchor module 119. The protrusions 306 provide two fixed attachment points which must be respectively aligned with two fixed anchoring points in the anchor module 119 for the predrilling module 300 to engage with anchor module 119. In the present embodiment, the protrusions 306 are positioned to align with anchor module 119 while the patient's bone 3 is in a closed configuration, thereby allowing the predrilling module 300 to engage with the patient's bone 3 and predrill holes 308 prior to opening the bone 3 (i.e. the protrusions 306 respectively align with the proximal 125a and distal 125b sections while they are adjacent one another). It is appreciated that in other embodiments, the protrusions 306 can be positioned to align with the anchor module 119 when the patient's bone is in the opened configurations (i.e. when the proximal 125a and distal 125b sections are space apart from one another across the opening in the patient's bone 3).

Although in the present embodiment a single mechanism 305 provides both the functions of securing and aligning predrilling module 300 relative to the patient's bone 3, it is appreciated that in other embodiments, different mechanisms can be provided to align and/or to secure predrilling module 300, and that separate mechanisms can be provided to respectively perform the alignment or attachment functions. For example, in some embodiments, predrilling module 300 can be secured to the patient's bone directly via fasteners. In some embodiments, the bone interface side 301 of predrilling module 300 can be shaped to have contours complementary in shape to the contours of a specific area of the patient's bone 3. In some embodiments, mechanism 305 can comprise a member configured to interface and/or insert into a hole or other feature formed in the patient's bone 3, for example in the opening formed along the planar cut.

The predrilling module 300 further comprises a handle member 313 which allows the module 300 to be more easily manipulated and positioned. In the present embodiment, the handle member 313 is a rigid elongated member extending from the body of the predrilling module 300 along a lengthwise axis and facilitates manipulation of the module 300 by hand. It is appreciated that in other embodiments, different types of handle members can be provided. For example, handle member can be removable and/or can comprise an interface for a positioning tool or guide. In the present embodiment, the handle member 313 has inscriptions provided thereon to identify the predrilling module 300 and/or to indicate the type of drill bits with which the predrilling module 300 is designed to cooperate.

Figure 9:
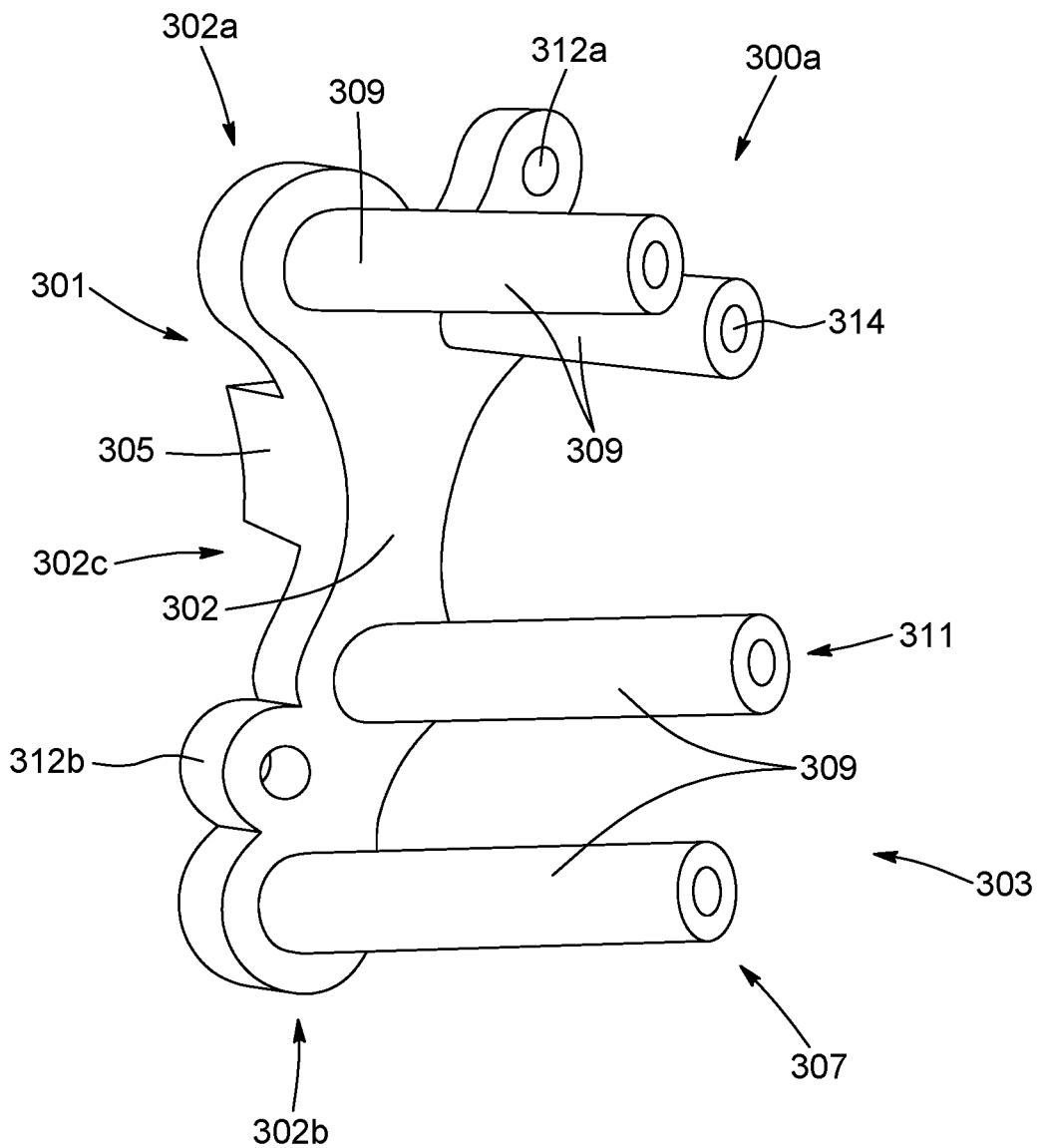
FIG. 9 is a perspective view of a predrilling module, according to an alternate embodiment in which the predrilling module is configured to drill holes for the fixation plate after an open wedge has been formed in the patient's bone.

Although in the illustrated embodiment the predrilling module 300 is configured to drill holes 308 prior to a change in the geometry of the patient's bone 3, it is appreciated that the predrilling module 300 can be configured differently according to the requirements of the surgical procedure. For example, as shown in FIG. 9, an embodiment of a predrilling module 300a is shown in which the module 300a is configured to drill holes 308 after the geometry of the patient's bone 3 has been surgically altered. In this embodiment, the predrilling module 300a is configured to span across opening 7 formed in the patient's bone 3, and position drill guides 307 to define drill holes 308 directly in their final position. More specifically, the predrilling module 300a has a body 302 substantially similar to a fixation plate which will ultimately be used to secure the opening 7 in the patient's bone 3. The bone 3 can thus be opened along planar cut 5 to form opening 7, and once the opening 7 is formed, the predrilling module 300 can be secured to the bone at the same position where the fixation plate will eventually be attached. The predrilling module 300 will thus have its drill guides 307 positioned exactly where the fastener apertures of fixation plate will eventually be positioned. Therefore, after drill holes 308 are formed, predrilling module 300 can be removed and replaced with fixation plate. Fixation plate can be positioned to align with the holes 308 and then secured in place via fasteners.

In the present embodiment, the body 302 of predrilling module 300 has a bone interface side 301 having a bone-contacting surface substantially conforming to a surface contour of the patient's bone 3 at a predetermined position. The body 302 is configured with a proximal section 302a for positioning adjacent a surface of the patient's bone 3 above opening 7, a distal section 302b for positioning adjacent a surface of the patient's bone 3 below opening 7, and an intermediate section 302c for spanning the opening 7. The attachment/alignment mechanism 305 comprises a wedge extending from bone interface side 301 on the intermediate section 302c of body 302, and configured to be inserted into the opening 7. As can be appreciated, wedge 305 can be sized and shaped according to the expected dimensions of the desired opening 7 according to a preoperative plan. It can further comprise contours matching inner surface contours of the opening 7, as will be described in more detail below in connection with the opening validator. The wedge 305 can thus allow predrilling module 300 to secure at a predetermined position relative to opening 7, while also validating that the bone 3 has been opened to the correct angle. Once module 300 has been correctly positioned, it can be secured in place relative to the patient's bone 3 before drilling is performed through drill guides 307. In the present embodiment, the body 302 comprises fastener apertures 312a, 312b in the proximal 302a and distal 302b sections to allow the body 302 to be secured directly to the patient's bone 3 via fasteners. It is appreciated, however, that other attachment mechanisms are possible. For example, the module 300 could secure to an anchor module already attached to the patient's bone 3 at the correct position.

Spreader Module

Figure 4A:
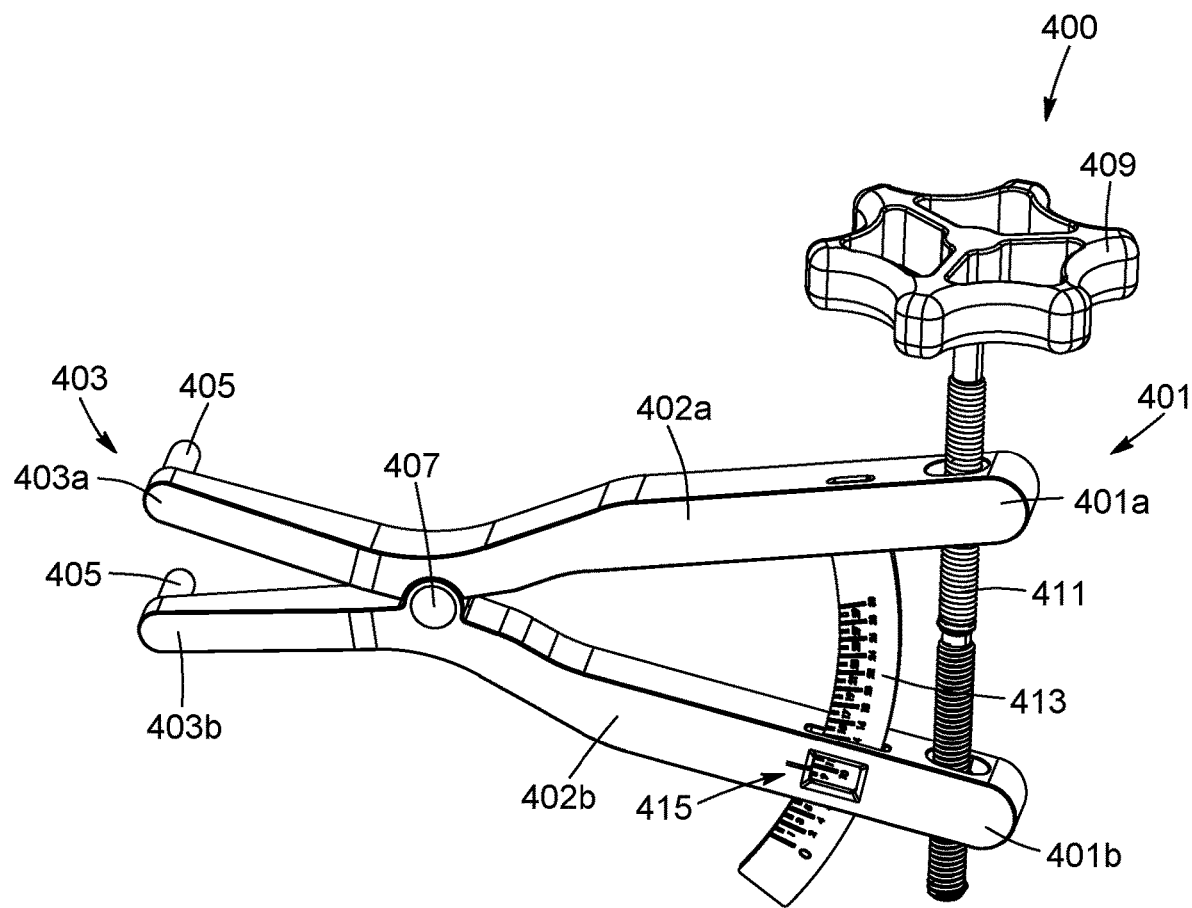
FIG. 4A is a perspective view of a spreading module, according to an embodiment.
Figure 4B:
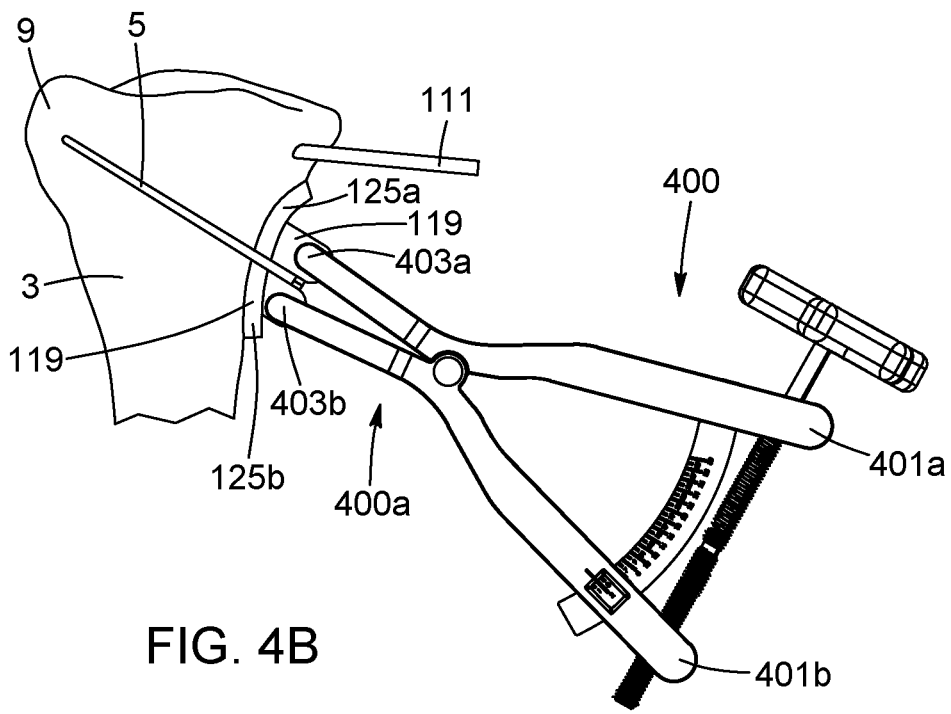
FIGS. 4B and 4C are side views showing operation of a spreading module respectively in a closed configuration and an open configuration.
Figure 4C:
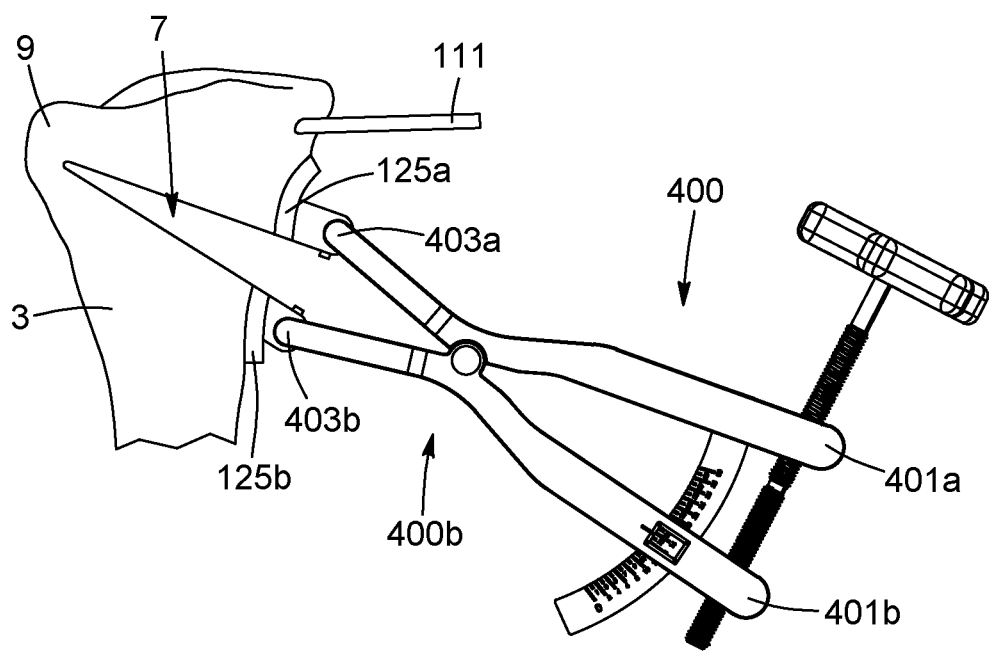

With reference now to FIGS. 4A, 4B and 4C, a spreader module 400 to assist in spreading the patient's bone 3 is shown according to an embodiment. In the present embodiment, the spreader module 400 is configured to open the patient's bone 3 along a planar cut 5 formed therein. The planar cut 5 is opened at an angle about a hinge 9, thereby defining an open wedge 7 in the patient's bone. The spreader module 400 is configured to operate in cooperation with anchor module 119 secured to the patient's bone 3, but it is appreciated that other configurations are possible. As can be appreciated, the spreader module 400 can be a generic tool, and need not be custom made according to the patient. Instead, the surgical guide 100 can be designed to cooperate with generic spreader module 400. Accordingly, spreader module 400 can be made out of any rigid material, according to any manufacturing process. However, it is appreciated that in some embodiments, the spreader module 400 can be custom designed for the patient and to conform to a specific geometry of the guide 100. In such embodiments, the spreader module 400 can be made from materials suitable for custom manufacturing, for example from the same 3D printed plastic from which the surgical guide 100 and corresponding modules are made.

In the present, spreader module 400 comprises an upper arm 402*a* and a lower arm 402*b* pivotally connected to one another via a hinge 407. As can be appreciated, spreader module 400 is generally configured as a double lever, with an effort end 401 and a load end 403, and hinge 407 acting as a fulcrum therebetween. More specifically, as effort ends 401*a*, 401*b* of upper and lower arms 402*a*, 402*b* are moved towards one another, upper and lower arms 402*a*, 402*b* pivot about hinge 407 causing load ends 403*a*, 403*b* to move away from one another. In other words, a force applied at effort end 401 causing ends 401*a* and 401*b* to converge is transferred to load end 403, causing load ends 403*a* and 403*b* to separate. It is appreciated that other configurations of spreader module 400 are possible, so long as it permits a separating force to be applied to load ends 403*a* and 403*b*. For example, in some embodiments, the spreader module 400 can be configured such that a spreading of effort ends 401*a*, 401*b* transfers a spreading force to load ends 403*a*, 403*b*. In other embodiments, different types of spreading mechanisms are possible.

In the present embodiment, force on effort end 401 is applied via a hand wheel 409. As wheel 409 is operated, screw mechanism 411 rotates and engages in threaded bores in effort ends 401*a*, 401*b*, thereby drawing effort ends 401*a*, 401*b* together or spreading them apart depending on the rotating direction of screw 411. As can be appreciated, in this configuration, a rotational force applied to wheel 409 is converted into a linear force which draws effort ends 401*a*, 401*b* together or spaces them apart. Moreover, the rotational force applied to and wheel 409 merely causes a change in spacing of effort ends 401*a*, 401*b*. A constant force does not need to be applied to wheel 409 to retain effort ends 401, 401*b* at a fixed spacing; instead, when no force is applied, the engagement of screw mechanism 411 retains arms 402 of spreader module 400 at their current angle, retaining effort ends 401*a*, 401*b* at a fixed spacing until force is applied to wheel 409. Spacing of effort ends 401*a*, 401*b* can thus be precisely controlled by hand, via small and/or measured rotational movements of hand wheel 409. It is appreciated, however, that a force controlling spacing of effort ends 401*a*, 401*b* can be applied via different mechanisms, and that such mechanisms need not necessarily be operated by hand. For example, in some embodiments, force can be applied via hydraulics or motors, and/or can be controlled electronically.

As mentioned above, spreader module 400 is configured to cooperate with anchor module 119 secured to the patient's bone 3. Spreading module 400 comprises an anchor interface 405 at load end 403 for interfacing with anchor 119 and transferring spreading force thereto. More specifically, in the present embodiment, the anchor interface 405 comprises protrusions or pins sized and shaped to engage in corresponding apertures in anchor module 119. A protrusion or pin at load end 403*a* of upper arm 402*a* is positioned to engage with proximal section 125*a* of anchor module 119, whereas a protrusion or pin at load end 403*b* or lower arm 402*b* is positioned to engage with distal section 125*b* of anchor module. In this configuration, arms 402*a*, 402*b* of spreader module independently engage in the distinct anchoring points 125*a*, 125*b*, allowing arms 402*a*, 402*b* to apply a spreading force thereon in opposite directions, and move anchoring points 125*a*, 125*b* away from one another.

In the present embodiment, the protrusions or pins extend from arms 402*a*, 402*b* substantially perpendicular therefrom, and along an axis substantially parallel to the pivot axis of hinge 407. As can be appreciated, in this configuration, spreader module 400 can engage with anchor 119 by sliding protrusions or pins of anchor interface 405 laterally into the corresponding apertures of anchor 119. A vertical spreading force can be subsequently applied to arms 402*a*, 402*b* without causing interface 405 to disengage. In the same manner, spreader module 400 can be easily disengaged from anchor 119 by sliding the protrusions or pins out along the lateral direction. As can be further appreciated, in this configuration, spreader module 400 can engage with anchor module 119 and operate along the lateral section of the patient's bone 3, leaving anterior section of the bone 3 clear so as to not interfere with subsequent steps in the surgical procedure. Apertures in anchor module 119 open on both anterior and lateral sides thereof, allowing the spreader module 400 to engage on either the anterior or lateral side of anchor module 119 depending on the requirements of the surgical procedure. It is appreciated, however, that in other embodiments, spreader module 400 can engage on other sides of anchor module 119, such as on its front side, and/or on top/bottom sides.

In the present embodiment, pins or protrusions of anchor interface 405 are substantially cylindrical and engage in substantially circular apertures in anchor module 119. As can be appreciated, in this configuration, pins or protrusions can rotate freely inside apertures of anchor module 119, allowing relative angular displacement of ends 403*a*, 403*b* relative to anchoring points 125*a*, 125*b* while engaged therein. It is appreciated, that in other embodiments, anchor interface 405 and/or anchor module 119 can comprise different engagement mechanisms. For example, in some embodiments, anchor interface 405 can be secured to anchor module 119 via fasteners. In some embodiments, ends 403*a*, 403*b* can key into anchoring points 125*a*, 125*b* at specific relative orientations, and/or pins or protrusions can be pivotally secured to ends 403*a*, 403*b* of arms 402*a*, 402*b*.

Spreader module 400 is operable to move between a closed configuration 400*a* and an opened configuration 400*b*. In the closed configuration 400*a*, anchor interface 405 on load ends 403*a*, 403*b* are substantially proximate one another and aligned with anchoring points 125*a*, 125*b* prior to spreading the patient's bone 3. In the opened configuration 400*b*, anchor interface 405 on load ends 403*a*, 403*b* are spaced apart from one another, and load end 403*a*, 403*b* are angled relative to one another at an opening angle. In the present embodiment, a gauge 413 is provided to indicate the magnitude of opening angle. The gauge 413 comprises a scale affixed to upper arm 402*a*, and movable through a corresponding aperture in lower arm 402*b*. A window 415 in lower arm 402*b* provides a visual indicator for reading scale. It is appreciated, however, that other gauge mechanisms are possible to indicate the magnitude of opening angle. In the present embodiment, gauge 413 is calibrated such that scale is zeroed when the spreader module 400 is in the closed configuration 400*a*. The opening angle indicated by gauge 413 can thus provide an accurate and precise indication of the opening angle of spreader module 400. In some embodiments, the gauge 413 can be further calibrated such that it corresponds to the opening angle about hinge 9 in patient's bone 3. In this configuration, the gauge can provide a precise and accurate indicate of opening angle of the open wedge 7 formed in the patient's bone, as the bone is opened along cut 5 using spreader module 400.

Although the module 400 is referred to herein as a "spreader" module, it is appreciated that it can be used not only to spread the patient's bone 3, but also to contract the patient's bone 3, for example as part of a closed-wedge osteotomy. In such procedures, the spreader module 400 can be operated to draw anchoring points 125*a*, 125*b* closer together, for example to close an open wedge 7 cut into the patient's bone 3. More particularly, spreader module 400 can engage with anchoring points 125*a*, 125*b* while in the opened configuration 400*b*, with the anchoring points 125*a*, 125*b* being positioned on opposite sides of an open wedge 7. The spreader module 400 can be subsequently operated towards the closed configuration 400*a* by turning hand wheel 409, thereby drawing anchoring points 125*a*, 125*b* together and closing the wedge 7.

While the above description provides examples of the embodiments, it will be appreciated that some features and/or functions of the described embodiments are susceptible to modification without departing from the spirit and principles of operation of the described embodiments. Accordingly, what has been described above has been intended to be illustrative and non-limiting and it will be understood by persons skilled in the art that other variants and modifications may be made without departing from the scope of the invention as defined in the claims appended hereto.

The invention claimed is:

1. A surgical guide assembly for performing an orthopedic surgery procedure, the assembly comprising:
   a body for securing to a patient's bone and comprising a drilling module interface; and
   a plurality of guide modules removably attachable to the body and comprising drilling modules removably securable to the body via the drilling module interface, the drilling modules comprising:
      a first drilling module adapted to guide a drilling tool to form a first set of drill holes in a first parallel orientation in a common plane; and
      a second drilling module adapted to guide the drilling tool to form a second set of drill holes in a second parallel orientation different from the first parallel orientation, and in the same common plane to weaken the patient's bone in preparation for forming a cut therein.

2. A surgical guide assembly for performing an orthopedic surgery procedure, the assembly comprising:
   a body for securing to a patient's bone; and
   a plurality of guide modules removably attachable to the body, each guide module being adapted to receive a corresponding surgical tool and to guide the corresponding surgical tool along a predetermined path during the orthopedic surgery procedure, the plurality of guide modules comprising at least two drilling modules removably securable to the body, each one of the at least two drilling modules including a plurality of drill guides for cooperating with at least one drill bit to guide a position, depth, and angle thereof for forming drill holes in the patient's bone in a predetermined configuration to weaken the patient's bone in preparation for forming a cut therein, wherein the body has a drill module interface adapted to selectively receive one of the at least two drilling modules for connection thereof to the body, and wherein the at least two drilling modules include a first drilling module having a first group of drill guides adapted to guide the at least one drill bit to form drill holes in a first parallel orientation in a common plane and a second drilling module having a second group of drill guides adapted to guide the at least one drill bit to form drill holes in a second parallel orientation different from the first parallel orientation, and in the same common plane.

3. The assembly according to claim 2, wherein the plurality of guide modules further includes a cutting module secured to the body, the cutting module including a slot sized and shaped to receive a corresponding osteotome therein, and configured to guide the osteotome to cut the patient's bone at a position, angle, and depth corresponding to an area of the patient's bone weakened by the at least two drilling modules.

4. The assembly according to claim 3, wherein the cutting module is positioned adjacent the patient's bone, and the drilling module is positioned adjacent the cutting module.

5. The assembly according to claim 4, wherein the slot is positioned in alignment with the drill guides to allow the drill guides to guide the at least one drill bit through the slot before entering the patient's bone.

6. The assembly according to claim 5, wherein at least one of the drilling modules is removably attached to the cutting module via at least one connecting member extending therebetween, each connecting member being severable to allow the drilling module to be removed from the cutting module.

7. The assembly according to claim 2, wherein the body includes an anchor module for anchoring the guide modules relative to the patient's bone, the anchor module including a removable module interface for selectively interfacing with one of the guide modules.

8. The assembly according to claim 7, wherein the removable module interface includes at least one aperture for receiving at least one corresponding protrusion extending from a corresponding guide module.

9. The assembly according to claim 8, wherein the body includes a first section and a second section detachably connected to the first section.

10. The assembly according to claim 9, wherein the first and second sections are independently securable relative to the patient's bone to allow one of the first and second sections to be removed from the patient's bone while the other one of the first and second sections remains secured to the patient's bone.

11. The assembly according to claim 7, wherein the anchor module comprises a proximal section positioned proximate a joint between the patient's bones, and a distal section spaced further away from the joint between the bones, the proximal and distal sections being separable from one another to allow them to move independently from each other while being secured to different sections of the patient's bone.

12. The assembly according to claim 11, further including a spreader module configured to operate in cooperation with the anchor module for opening the patient's bone along a planar cut formed therein.

13. The assembly according to claim 12, wherein the spreader module comprises an upper arm and a lower arm pivotally connected to one another via a hinge, each one of the upper and lower arms having a load end and an effort end, the upper and lower arms being pivotable such that movement of the effort ends of the upper and lower arms towards one another moves the load ends of the upper and lower arms away from each other.

14. The assembly according to claim 13, wherein the upper arm includes a protrusion for engaging with the proximal section of the anchor module and the lower arm includes a protrusion for engaging with the distal section of the anchor module.

15. The assembly according to claim 7, wherein the plurality of guide modules further includes a predrilling module for predrilling holes in the patient's bone for receiving fasteners to secure at least one of a plate and an implant to the patient's tibia bone.

16. The assembly according to claim 15, wherein the predrilling module comprises an attachment interface for interfacing with the removable module interface of the anchor module to attach the predrilling module to the anchor module, the attachment interface allowing the predrilling module to be positioned in only one position when attached to the anchor module.

17. The assembly according to claim 2, wherein at least some of the plurality of guide modules are removably and interchangeably attachable to the body.

18. The assembly according to claim 2, wherein the body includes a bone interface side for abutting against the patient's bone, the bone interface side including a surface having contours complementary in shape to the surface contours of a predetermined area of the patient's bone.

19. The assembly according claim 2, wherein the body is custom made according to an anatomy of the patient's bone so as to be patient-specific.

20. The assembly according to claim 2, wherein the body is made of a biocompatible material.

21. The assembly according to claim 2, wherein the plurality of guide modules are made of a biocompatible material.

22. The surgical guide assembly according to claim 2, wherein the orthopedic surgery procedure is a knee osteotomy procedure and the patient's bone is a tibia bone.

\* \* \* \* \*

UNITED STATES PATENT AND TRADEMARK OFFICE
CERTIFICATE OF CORRECTION

Page 1 of 1

PATENT NO. : 11,589,876 B2
APPLICATION NO. : 16/610446
DATED : February 28, 2023
INVENTOR(S) : Jean Robichaud et al.

It is certified that error appears in the above-identified patent and that said Letters Patent is hereby corrected as shown below:

On the Title Page

At item (54), and in the Specification, Column 1, Line 1, "SURGICAL GUIDE ASSEMBLY FOR PERFORMING A KNEE OSTEOTOMY PROCEDURE" should be -- SURGICAL GUIDE ASSEMBLY FOR PERFORMING AN ORTHOPEDIC PROCEDURE --.

In the Claims

At Column 20, Line 57, "bone." should be -- bones. --.

At Column 21, Line 12, "tibia bone." should be -- bone. --.

At Column 22, Line 9, "according" should be -- according to --.

Signed and Sealed this
Thirtieth Day of July, 2024

Katherine Kelly Vidal
*Director of the United States Patent and Trademark Office*